United States Patent [19]

Hunkeler et al.

[11] Patent Number: 4,863,920
[45] Date of Patent: Sep. 5, 1989

[54] IMIDAZODIAZEPINE DERIVATIVES FOR TREATMENT OF DISORDERS OF THE CENTRAL NERVOUS SYSTEM

[75] Inventors: Walter Hunkeler, Magden; Emilio Kyburz, Reinach, both of Switzerland; Marc Meier, Village-Neuf, France

[73] Assignee: Hoffmann-La Roche Inc., Nutley, N.J.

[21] Appl. No.: 163,441

[22] Filed: Mar. 3, 1988

[30] Foreign Application Priority Data

Mar. 10, 1987 [CH] Switzerland .................. 880/87
Jan. 8, 1988 [CH] Switzerland .................. 59/88

[51] Int. Cl.$^4$ .................. A61K 31/33; C07D 487/02
[52] U.S. Cl. .................. 514/219; 540/498; 540/493; 514/220
[58] Field of Search .................. 540/498, 493, 487; 514/220, 219

[56] References Cited

U.S. PATENT DOCUMENTS

| | | | |
|---|---|---|---|
| 4,280,957 | 7/1981 | Walser et al. | 540/498 |
| 4,316,839 | 2/1982 | Gerecke et al. | 540/498 |
| 4,352,818 | 10/1982 | Hunkeler et al. | 540/498 |
| 4,775,671 | 10/1988 | Hunkeler et al. | 540/498 |

FOREIGN PATENT DOCUMENTS

| | | | |
|---|---|---|---|
| 0109921 | 5/1984 | European Pat. Off. | 540/498 |
| 0202441 | 11/1986 | European Pat. Off. | 540/498 |

OTHER PUBLICATIONS

J. March, "Advanced Organic Chemistry: Reaction Mechanisms and Structure", McGraw-Hill Book Co., New York (1968).
Morrison and Boyd, "Organic Chemistry" (1976).
Hendrickson et al., "Organic Chemistry", 3d. Edition, McGraw-Hill, Kogakusha, Tokyo (1970).
Litter, "Pharmacology", 6th Edition, El Ateneo, Buenos Aires (1980).
Goodman and Gilman, "The Pharmacological Basis of Therapeutics", 6th Edition, MacMillan & Co. (1980).
The Merck Index, 10th Edition (1983).

*Primary Examiner*—Mary C. Lee
*Assistant Examiner*—Robert C. Whittenbaugh
*Attorney, Agent, or Firm*—Jon S. Saxe; Bernard S. Leon; Richard J. Mazza

[57] ABSTRACT

A compound for treating disorders of the central nervous system, which is of the formula

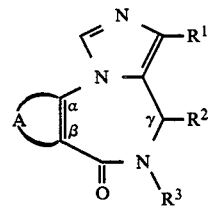

wherein A taken together with the two carbon atoms denoted by α and β is one of the following groups:

$R^1$ is one of the following groups:

$$-CH=CH-R^6 \quad (d)$$

and $$-C\equiv C-R^6, \quad (e)$$

$R^2$ is hydrogen, $R^3$ is lower alkyl, or $R^2$ and $R^3$ together are dimethylene or trimethylene, $R^4$ and $R^5$ are independently hydrogen, halogen, trifluoromethyl or lower alkyl, and $R^6$ is hydrogen, halogen, aryl or a saturated lower hydrocarbon group which is optionally mono- or di-substituted by hydroxy, lower alkoxy, ($C_3$-$C_7$)-cycloalkyl or oxo, wherein the compound has the (S)- or (R,S)-configuration with reference to the carbon atom denoted by γ when $R^2$ and $R^3$ together are dimethylene or trimethylene and, further, the double bond present in group (d) has the E- and/or Z-configuration when $R^6$ is different from hydrogen.

33 Claims, No Drawings

IMIDAZODIAZEPINE DERIVATIVES FOR TREATMENT OF DISORDERS OF THE CENTRAL NERVOUS SYSTEM

DESCRIPTION OF THE INVENTION

The present invention relates to imidazodiazepine derivatives. In particular, it concerns imidazodiazepine derivatives of the formula

I wherein
A taken together with the two carbon atoms denoted by α and β is one of the following groups:

(a)  (b)  (c)

$R^1$ is one of the following groups:

$-CH=CH-R^6$ (d)

and $-C\equiv C-R^6$, (e)

$R^2$ is hydrogen and $R^3$ is lower alkyl, or $R^2$ and $R^3$ together are dimethylene or trimethylene, $R^4$ and $R^5$ are independently hydrogen, halogen, trifluoromethyl or lower alkyl, and
$R^6$ is hydrogen, halogen, aryl or a saturated lower hydrocarbon group which is optionally mono- or disubstituted by hydroxy, lower alkoxy, ($C_3$-$C_7$)-cycloalkyl or oxo, whereby the compounds of formula I have the (S)- or (R,S)-configuration with reference to the carbon atom denoted by γ when $R^2$ and $R^3$ together are dimethylene or trimethylene and whereby the double bond present in group (d) has the E- and/or Z-configuration when $R^6$ is different from hydrogen.

These compounds are characterized by valuable pharmacodynamic properties and are useful as therapeutic agents for the conditions described below.

The present invention thus comprises the compounds of formula I, above, which are useful in the control or prevention of illnesses, especially in the control or prevention of convulsions, anxiety states, stress conditions, excitation states and sleep disorders and/or in the partial or complete selective antagonism of some or all activities which 1,4-benzodiazepines having tranquillizing activity or other substances display via the central benzodiazepine receptors. Another aspect of the invention comprises therapeutic agents containing a compound of formula I and an inert carrier.

The term "lower" is used herein to denote residues and compounds with up to 7, preferably up to 4, carbon atoms. The term "lower alkyl" denotes straight-chain or branched saturated hydrocarbon residues with a maximum of 7, preferably a maximum of 4, carbon atoms such as methyl, ethyl, n-propyl, isopropyl, n-butyl, isobutyl, s-butyl, t-butyl and the like. The term "lower alkoxy" denotes lower alkyl residues in the sense of the previous definition of the term "lower alkyl" which are attached via an oxygen atom. The term "aryl" denotes monocyclic aromatic hydrocarbon residues which can be substituted by lower alkyl, lower alkoxy, halogen, and so forth. Unless indicated otherwise, the term "halogen" denotes the four halogens: fluorine, chlorine, bromine and iodine.

The term "saturated hydrocarbon group" denotes open-chain and cyclic groups and combinations thereof. The open-chain groups can be straight-chain or branched. Examples of saturated lower hydrocarbon groups are: methyl, ethyl, i-propyl, t-butyl, 3-pentyl, cyclopropyl, cyclobutyl, cyclopentyl, cyclopropylmethyl, dicyclopropylmethyl and 1-cyclopropylethyl. Examples of saturated lower hydrocarbon residues which are mono- or disubstituted by hydroxy, lower alkoxy, ($C_3$-$C_7$)-cycloalkyl or oxo are: hydroxymethyl, methoxymethyl, dimethoxymethyl, 1-hydroxyethyl, 1-methoxyethyl, 1-hydroxypropyl, 2-hydroxy-2-propyl, 2-methoxy-2-propyl, 2-ethoxy-2-propyl, 3-hydroxy-3-pentyl, 1-hydroxy-1-cyclobutyl, 1-hydroxy-1-cyclopentyl, 1-methoxy-1-cyclopentyl, 1-oxoethyl and dicyclopropylhydroxymethyl.

When $R^1$ in formula I is a group of formula (d), then it stands, for example, for vinyl, 1-propenyl, 1-pentenyl or 2-chlorovinyl. However, $R^1$ in formula I preferably is a residue of formula (e). $R^6$ preferably is hydrogen, lower alkyl, lower hydroxy-alkyl, lower alkoxyalkyl, ($C_3$-$C_7$)-cycloalkyl, hydroxy-($C_4$-$C_7$)-cycloalkyl, lower alkoxy-($C_4$-$C_7$)-cyclo-alkyl, ($C_3$-$C_7$)-cycloalkyl-lower alkyl, ($C_3$-$C_7$)-cycloalkyl-lower hydroxyalkyl or ($C_3$-$C_7$)-cycloalkyl-lower alkoxyalkyl. In a particularly preferred embodiment, $R^6$ is hydrogen, lower alkyl, lower 1-hydroxyalkyl, lower 1-alkoxyalkyl, ($C_3$-$C_7$)-cycloalkyl, 1-hydroxy-($C_4$-$C_7$)-cycloalkyl, 1-(lower alkoxy)-($C_4$-$C_7$)-cycloalkyl or 1[($C_3$-$C_7$)-cycloalkyl]-lower 1-hydroxyalkyl, especially lower alkyl, lower 1-hydroxyalkyl or ($C_3$-$C_7$)-cycloalkyl, for example, methyl, ethyl, i-propyl, t-butyl, 3-pentyl, hydroxymethyl, 1-hydroxyethyl, 1-hydroxypropyl, 2-hydroxy-2-propyl, 3-hydroxy-3-pentyl or cyclopropyl.

When $R^2$ is hydrogen and $R^3$ is lower alkyl, then $R^3$ preferably is methyl. When $R^2$ and $R^3$ together are dimethylene or trimethylene, then the carbon atom denoted by γ preferably has the (S)-configuration.

When A is a residue of formula (a), then preferably one of $R^4$ and $R^5$ is hydrogen and the other is hydrogen or halogen. Thus, for example, $R^4$ and $R^5$ both are hydrogen or $R^4$ is hydrogen and $R^5$ is fluorine, or $R^4$ is chlorine and $R^5$ is hydrogen.

Preferred compounds of formula I within the scope of the present invention are:

7-Chloro-4,5-dihydro-5-methyl-3-(1-propynyl)-6H-imidazo[1,5-a][1,4]benzodiazepin-6-one;

7-chloro-4,5-dihydro-3-(3-hydroxy-3-methyl-1-butynyl)-5-methyl-6H-imidazo[1,5-a][1,4]benzodiazepin-6-one;

7-bromo-4,5-dihydro-3-(3-hydroxy-3-methyl-1-butynyl)-5-methyl-6H-imidazo[1,5-a][1,4]benzodiazepin-6-one;

7-chloro-4,5-dihydro-3-(3-hydroxy-1-butynyl)-5-methyl-6H-imidazo[1,5-a][1,4]benzodiazepin-6-one;

4,5-dihydro-5-methyl-3-(1-propynyl)-6H-imidazo[1,5-a][1,4]benzodiazepin-6-one;

7-chloro-4,5-dihydro-5-methyl-3-(3-methyl-1-butynyl)-6H-imidazo[1,5-a][1,4]benzodiazepin-6-one;

7-chloro-4,5-dihydro-3-(3-hydroxy-1-propynyl)-5-methyl-6H-imidazo[1,5-a][1,4]benzodiazepin-6-one; and 7-chloro-3-(cyclopropylethynyl)-4,5-dihydro-5-methyl-6H-imidazo[1,5-a][1,4]benzodiazepin-6-one.

The compounds of formula I can be made by the following processes:

(a) reacting a compound of the formula

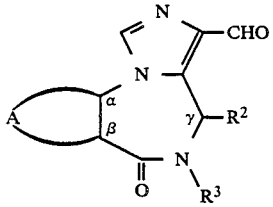

II wherein A, $R^2$ and $R^3$ have the above meanings, with a compound of the general formula

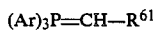

$(Ar)_3P=CH-R^{61}$   III wherein $R^{61}$ is hydrogen, halogen, aryl or a saturated lower hydrocarbon group which is optionally mono- or disubstituted by lower alkoxy, $(C_3-C_7)$-cycloalkyl or oxo and Ar is an aryl residue; or (b) dehydrohalogenating a compound of the formula

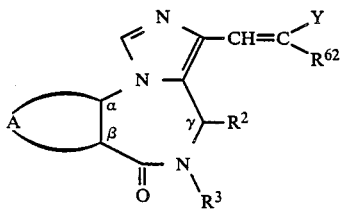

IV wherein $R^{62}$ is hydrogen or halogen and Y is halogen, and A, $R^2$ and $R^3$ have the above meanings; or (c) treating a compound of formula I in which $R^1$ is group (e) and $R^6$ is hydrogen, with an agent yielding a saturated lower hydrocarbon residue which is optionally mono- or disubstituted by hydroxy, lower alkoxy, $(C_3-C_7)$-cycloalkyl or oxo, or an aryl residue or halogen; or (d) reacting a compound of the formula

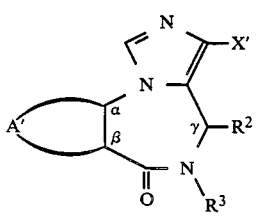

VI wherein $R^2$ and $R^3$ have the above meanings and X' is bromine or iodine and A' is a residue of formula (a), (b) or (c), with the proviso that where A' is a residue of formula (a) and $R^4$ and/or $R^5$ is halogen, this halogen is fluorine or chlorine when X' is bromine and is fluorine, chlorine or bromine when X' is iodine, with a compound of the formula

$HC\equiv C-R^{64}$   VII wherein $R^{64}$ is hydrogen, aryl or a saturated lower hydrocarbon group which is optionally mono- or disubstituted by hydroxy, lower alkoxy, $(C_3-C_7)$-cycloalkyl or oxo; or (e) cleaving off the protecting group from a compound of the formula

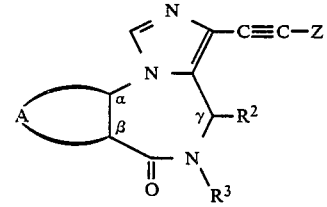

VIII wherein $R^2$, $R^3$ and A have the above meanings and Z is a protecting group; or (f) replacing the amino group in a compound of the formula

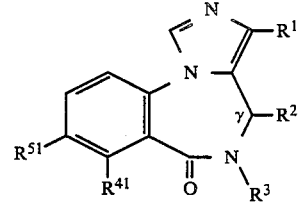

IX wherein $R^1$, $R^2$ and $R^3$ have the above meanings and one of $R^{41}$ and $R^{51}$ is amino and the other is hydrogen, halogen, trifluoromethyl or lower alkyl, by a hydrogen or halogen atom; or (g) reducing a compound of formula I in which $R^1$ is a residue of formula (e) and in which, where A is a residue of formula (a), $R^4$ and/or $R^5$ are not iodine, to the corresponding compound of formula I in which $R^1$ is a residue of formula (d); or (h) treating a compound of formula I in which $R^1$ is a residue of formula (d) or (e) and $R^6$ is a saturated lower hydrocarbon group which is substituted by hydroxy with an agent yielding a lower alkyl residue; or (i) reducing the carbonyl group in a compound of formula I in which $R^1$ is group (d) or (e) and $R^6$ is a saturated lower hydrocarbon group which is substituted by oxo.

Process aspect (a) yields compounds of formula I in which $R^1$ is group (d), but in which $R^6$ can have only those meanings which have been given above for $R^{61}$ in connection with formula III. The compounds of formula II which are used as starting materials are known or can be prepared readily according to methods which are known and which are familiar to those skilled in the art. Moreover, several of the Examples hereinafter contain detailed information concerning the preparation of specific compounds of formula II. The compounds of formula III are conveniently prepared in situ, from corresponding phosphonium halides such as methyltriphenylphosphonium bromide, ethyltriphenylphosphonium bromide, butyltriphenylphosphonium bromide, chloromethyltriphenylphosphonium chloride, and the like and a strong base such as sodium amide, butyllithium, and the like.

For example, the reaction can be carried out by placing the respective phosphonium halide such as ethyltriphenylphosphonium bromide in an organic solvent which is inert under the reaction conditions, such as tetrahydrofuran, ether, N,N-dimethylformamide, toluene or the like, and then adding thereto an approximately equimolar amount or a slight excess of a suitable strong base, for example, by adding dropwise a butyllithium solution in an organic solvent which is inert under the reaction conditions, such as n-hexane or the like.

According to another embodiment, the preparation of the starting materials of formula III is conveniently effected starting from equimolar mixtures of sodium amide and a phosphonium halide such as methyltriphenylphosphonium bromide, butyltriphenylphosphonium bromide, chloromethyltriphenylphosphonium chloride and the like, some of which are commercially available. Such mixtures can be used directly by taking them up in an organic solvent which is inert under the reaction conditions, such as tetrahydrofuran, ether, N,N-dimethylformamide, toluene, dioxane or the like. The solution or suspension containing a compound of formula III, which has been obtained according to the previously described methods, is then treated with a compound of formula II. In this case it is convenient to add the compound of formula II portionwise in solid form or to add dropwise a solution of a compound of formula II in an organic solvent which is inert under the reaction conditions, such as tetrahydrofuran, dioxane, ether or the like. Depending on the nature of the compounds used as reaction components and of the solvent or solvent mixture used as the reaction medium, the reaction of the compounds of formula III with the compounds of formula II is effected at or below or above room temperature. In general, the reaction temperature conveniently lies in a range of about −50° to about +50° C. As a rule, the reaction time varies between about a half hour and a few hours.

Process aspect (b) yields compounds of formula I in which $R^1$ is group (e), but in which $R^6$ can only be hydrogen or halogen. The dehydrohalogenation is conveniently effected by means of a base, for example, with an organic base which is as little nucleophilic as possible, thus conveniently with potassium tert.-butylate or the like, or with a bicyclic compound such as 1,8-diazabicyclo[5.4.0]undec-7-ene, 1,5-diazabicyclo[4.3.0]-non-5-ene or the like, or also with an inorganic base such as sodium hydride, sodium hydroxide or the like. Furthermore, the dehydrohalogenation is conveniently effected in an organic solvent which is inert under the reaction conditions, such as N,N-dimethylformamide, dimethyl sulphoxide, tetrahydrofuran, tert.-butanol or the like, at an elevated temperature, conveniently at the boiling temperature of the reaction system. It can also be effected by means of sodium amide in liquid ammonia or by means of a solution of sodium in a lower alcohol such as methanol, and it takes several hours, for example, about 3 to about 8 hours.

In accordance with process aspect (c), a compound of formula I in which $R^1$ is group (e) and $R^6$ is hydrogen is first deprotonized by means of a strong base such as sodium hydride, potassium tert.-butylate, butyllithium or the like, which is conveniently effected in an organic solvent inert under the reaction conditions, such as N,N-dimethylformamide, toluene, tetrahydrofuran or the like. Sodium amide in liquid ammonia or sodium hydroxide in a lower alcohol such as methanol can, however, also be used for the deprotonization. There is subsequently added thereto the agent yielding the desired residue, the nature of which depends, of course, on the desired residue to be introduced. For the introduction of a lower alkyl group there is used, for example, a lower alkyl halide such as methyl iodide, a lower dialkyl sulphate or a lower alkyl ester of a sulphonic acid such as methanesulphonic acid, benzenesulphonic acid, p-toluenesulphonic acid or p-bromobenzenesulphonic acid, etc. A lower alkoxy-lower alkyl residue, a ($C_4$–$C_7$)-cycloalkyl residue or a ($C_3$–$C_7$)-cycloalkyl-lower alkyl residue can be introduced in an analogous manner, for example, by means of chlorodimethyl ether, cyclohexyl bromide, cyclopropylmethyl bromide and the like. In order to introduce a hydroxyl-containing residue in which the hydroxy group is situated in the α-position, a corresponding carbonyl compound can be used. Thus, for example, a hydroxymethyl group is introduced by means of formaldehyde, a 2-hydroxy-2-propyl group is introduced by means of acetone, and so forth. A β-hydroxy-alkyl group can be introduced conveniently by means of a corresponding epoxide, a 2-hydroxyethyl group can thus be introduced by means of ethylene oxide, and a halogen atom can be introduced by means of elementary halogen. The reaction conditions depend, of course, on the nature of the reagent which is used for the introduction of each of the desired residues. If this reagent is, for example, methyl iodide, then the reaction is conveniently effected in an organic solvent which is inert under the reaction conditions, such as N,N-dimethylformamide, tetrahydrofuran, toluene, dioxane, dimethyl sulphoxide or the like, at room temperature, for several, e.g., 2–5, hours.

The reaction of compounds of formulae VI and VII in accordance with process aspect (d) is effected in the presence of a palladium(II) salt such as palladium chloride or palladium acetate, of an organophosphine such as triphenylphosphine, of copper(I) iodide and of a secondary or tertiary amine such as diethylamine or triethylamine. In place of a palladium(II) salt and an organophosphine there can also be used a suitable corresponding complex such as, for example, bis-(triphenylphosphine)-palladium(II) dichloride. As the solvent there can be used the mentioned secondary or tertiary amine itself, a halogenated hydrocarbon such as methylene chloride or the like, N,N-dimethylformamide or the like. As the compound of formula VII there is used, for example, propyne, 3,3-dimethyl-1-butyne, phenylacetylene, propargyl alcohol, 2-methyl-3-butyn-2-ol, or the like. Depending on the nature of the compound of formula VII which is used, the reaction is effected under pressure and at temperatures in a range between about room temperature and about 120° C. The reaction time amounts to about 1 to about 70 hours, depending on the remaining reaction parameters. The starting materials of formula VI are known or can be prepared readily according to methods which are known to those skilled in the art. Moreover, some of the Examples hereinafter contain detailed information concerning the preparation of certain compounds of formula VI.

Process aspect (e) yields compounds of formula I in which $R^1$ is a residue of formula (e) and $R^6$ is hydrogen. As protecting groups which are denoted by Z in formula VIII there come into consideration, of course, only those residues which can be removed selectively without affecting other groups present in the molecule. Residues which satisfy these requirements and methods for their selective removal are familiar to the person skilled in the art. There are suitable, for example, trialkylsilyl groups such as trimethylsilyl, α-hydroxyalkyl groups such as 2-hydroxy-2-propyl, and so forth. The cleavage of trialkyl-silyl groups can be effected, for example, by means of potassium fluoride in water, by means of an alkali metal hydroxide such as potassium hydroxide in a lower alkanol such as ethanol, and/or water, or the like, and the cleavage of groups such as 2-hydroxy-2-propyl can be effected conveniently under alkaline conditions, for example, by means of an alkali metal hydroxide such as sodium hydroxide, an alkali metal hydride such as sodium hydride, or the like, in an organic solvent which is inert under the reaction conditions, for example in an aromatic hydrocarbon such as toluene, benzene, xylene, or the like. Those starting materials of formula VIII which do not fall under the scope of formula I are also novel and are likewise an object of the present invention. The preparation of such compounds can be effected in an analogous manner to the manufacture of corresponding compounds of formula I, for example, in analogy to process aspect (d).

The replacement of an amino group by a halogen atom in accordance with process aspect (f) can be effected by converting the amino compound of formula IX into a corresponding diazonium salt and reacting this, optionally without previous isolation, with a halide, for example, with a chloride or bromide, in the presence of a copper(I) salt. The preparation of corresponding iodo compounds is effected in an analogous manner, but the presence of a copper(I) salt is not necessary. Corresponding fluoro compounds are conveniently prepared via the corresponding diazonium tetrafluoroborate, for example by irradiation with UV light. The previously mentioned reactions are carried out in aqueous solutions at temperatures of about −10° C. to about room temperature.

The replacement of the amino group by a hydrogen atom in accordance with process aspect (f) can be carried out by reducing a corresponding diazonium salt, for example, by heating in a cyclic ether such as tetrahydrofuran or dioxane or in ethanol, N,N-dimethylformamide or the like, preferably at the boiling temperature of the reaction mixture. However, an amine of formula IX can also be reacted with t-butyl nitrite, isopentyl nitrite, and the like, in a cyclic ether such as tetrahydrofuran or dioxane, preferably at the boiling temperature of the reaction mixture.

The starting materials of formula IX are novel and are likewise an object of the present invention. Their preparation is effected by reducing corresponding nitro compounds and these, in turn, can be obtained in analogy to the preparation of corresponding compounds of formula I.

In accordance with process aspect (g), a carbon-carbon triple bond is partially reduced to a carbon-carbon double bond. Such a partial reduction can be carried out according to methods which are customary and are familiar to those skilled in the art, conveniently by hydrogenation in the presence of a partially inactivated catalyst, for example, in the presence of a palladium catalyst pre-treated with quinoline and/or lead. The partial hydrogenation is conveniently effected at room temperature and atmospheric pressure in an organic solvent which is inert under the reaction conditions, for example, in ethyl acetate, methanol, N,N-dimethylformamide, dichloromethane, or the like.

In accordance with process aspect (h), a hydroxy group is converted into a lower alkoxy group. This is thus an etherification of a hydroxy group, and methods for carrying out such an etherification are known to those skilled in the art. The etherification in accordance with the invention is conveniently effected by means of a lower alkyl halide such as methyl iodide, a lower dialkyl sulphate or a lower alkyl ester of an organic sulphonic acid such as methanesulphonic acid, benzenesulphonic acid, p-toluenesulphonic acid, p-bromobenzenesulphonic acid, and the like. The reaction is conveniently carried out in the presence of a base, for example, an alkali metal hydroxide such as sodium hydroxide, and in the presence of an organic solvent which is inert under the reaction conditions, for example, in N,N-dimethylformamide, dimethyl sulphoxide, toluene, and the like.

In accordance with process aspect (i), a carbonyl group is reduced to the corresponding alcohol group. This reduction can be carried out according to methods which are known to those skilled in the art. As the reducing agent there come into consideration, for example, an alkali metal borohydride such as sodium borohydride. Suitable solvents are, for example, lower alcohols, such as methanol and ethanol, and dimethylformamide and mixtures thereof. The reduction is conveniently carried out at room temperature.

As mentioned earlier, the compounds of formula I are novel. They possess valuable pharmacodynamic properties and have only a low toxicity. They have as a common characteristic a pronounced affinity to the central benzodiazepine receptors and have either pronounced anxiolytic, anticonvulsant, muscle relaxant and sedative-hypnotic properties and/or they partially or completely selectively antagonize some or all activities which 1,4-benzodiazepines having tranquillizing activity or other substances display via the central benzodiazepine receptors.

The affinity of compounds of formula I to the central benzodiazepine receptors was determined according to the method described in Life Science 20, 2101–2110 (1977) and Science 198, 849–851 (1977). According to this method, the inhibition of the binding of tritiated diazepam at the specific benzodiazepine receptors in the cerebral cortex by the respective test substances is ascertained. The $IC_{50}$ ("50% inhibiting concentration") is that concentration of the respective test substance which brings about a 50 percent inhibition of the specific binding of the tritiated diazepam at the specific benzodiazepine receptors in the cerebral cortex.

The central properties of the compounds of formula I in accordance with the invention can be determined, for example, in the antipentetrazole animal model which is described hereinafter and which is generally recognized for recording anticonvulsant properties.

In this animal model, the compound under investigation is administered orally to female rats weighing 60–80 g and 30 minutes later there are administered i.p. 120 mg/kg of pentetrazole, which causes emprosthotonus and tonic stretchings of the fore and/or hind limbs in unprotected experimental animals 1–4 minutes after the injection. Ten experimental animals are used per dosage of test substance. After counting the protected experimental animals the $ED_{50}$ is determined according to the Probit method. The $ED_{50}$ is that dosage which protects 50% of the experimental animals from the spasmodic seizures caused by pentetrazole.

One of the typical properties of 1,4-benzodiazepines having tranquillizing activity in animal experiments is their pronounced anticonvulsant activity which can be demonstrated, for example, in the known and generally recognized pentetrazole test. This property was used to elaborate the test described hereinafter which permits the investigation of compounds capable of antagonizing the central properties of 1,4-benzodiazepines having tranquillizing activity.

In this animal model there are administered to mice one hour before the pentetrazole (120 mg/kg, i.p.) 5 mg/kg (i.p.) of diazepam (i.e. a supramaximal dosage which in the pentetrazole test on more than 900 mice protected all experimental animals from spasmodic seizures) and the compound to be tested was administered p.o. 15 minutes before the pentetrazole. The antagonistic activity of the compounds investigated, that is, their capability to counteract the effect of the diazepam in the pentetrazole test, is determined by counting the mice which suffer spasmodic seizures in this test. The $ED_{50}$ denotes the amount of the respective test compound in mg/kg (p.o.) which in 50% of the animals counteracts the diazepam effect in the above test.

The results which have been obtained with representative members of the class of compound defined by formula I in the experiments described previously are compiled in the following Table. Moreover, the Table contains data concerning the acute toxicity of some of these compounds ($LD_{50}$ in mg/kg in the case of single oral administration to rats).

| Compound | Affinity to benzo- diazepine receptors IC 50, nmol/l | Antipem- tetrazole test ED 50 mg/kg p.o. | Antagonism of diazepam ED 50 mg/kg p.o. | Toxicity LD 50 mg/kg p.o. |
| --- | --- | --- | --- | --- |
| A | 4.5 | | 0.24 | 312–625 |
| B | 24 | | 1.5 | 312–625 |
| C | 2.3 | | 0.36 | >5000 |
| D | 2.4 | 1.5 | >50 | >4000 |
| E | 2.0 | 0.29 | | 500–1000 |
| F | 7.6 | | 1.2 | 1250–2500 |

A = 7-Chloro-3-ethynyl-4,5-dihydro-5-methyl-6H—imidazo [1,5-a][1,4]benzodiazepin-6-one
B = 3-Ethynyl-8-fluoro-4,5-dihydro-5-methyl-6H—imidazo [1,5-a][1,4]benzodiazepin-6-one
C = 7-Chloro-4,5-dihydro-5-methyl-3-(1-propynyl) 6H—imidazo-[1,5-a][1,4]benzodiazepin-6-one
D = (S)-8-Chloro-1-ethynyl-11,12,13,13a-tetrahydro-9H—imidazo[1,5-a]pyrrolo[2,1-c][1,4]benzodiazepin-9-one
E = 7-Bromo-4,5-dihydro-3-hydroxy-3-methyl-1-butynyl)-5-methyl-6H—imidazo[1,5-a][1,4]benzodiazepin-6-one
F = 7-Chloro-4,5-dihydro-5-methyl-3-vinyl-6H—imidazo-[1,5-a][1,4]benzodiazepin-6-one.

A selective antagonistic component, as can be demonstrated in the case of many of the compounds of formula I, is of great therapeutic significance in that it permits the use of desired properties (for example, anxiolytic or anti-convulsant activity) of the substances in accordance with the invention while repressing the additional properties (for example, sedative, muscle relaxant and the activities which disturb motoric coordination) which are undesired in certain cases of administration.

The compounds of formula I can be used as medicaments, for example, in the form of pharmaceutical preparations. The pharmaceutical preparations can be administered orally, for example, in the form of tablets, coated tablets, dragees, hard and soft gelatine capsules, solutions, emulsions or suspensions. The administration can, however, also be carried out rectally, for example, in the form of suppositories, or parenterally, for example, in the form of injection solutions.

For the preparation of pharmaceutical preparations the compounds of formula I can be processed with pharmaceutically inert, inorganic or organic carriers. As such carriers there can be used for tablets, coated tablets, dragees and hard gelatine capsules, for example, lactose, maize starch or derivatives thereof, talc, stearic acid or its salts and the like. Suitable carriers for soft gelatine capsules are, for example, vegetable oils, waxes, fats, semi-solid and liquid polyols and the like. Depending on the nature of the active substance no carriers are, however, generally required in the case of soft gelatine capsules. Suitable carriers for the manufacture of solutions and syrups are, for example, water, polyols, saccharose, invert sugar, glucose and the like. Suitable carriers for injection solutions are, for example, water, alcohols, polyols, glycerine, vegetable oils and the like. Suitable carriers for suppositories are, for example, natural or hardened oils, waxes, fats, semi-liquid or liquid polyols and the like.

The pharmaceutical preparations can also contain preserving agents, solubilizing agents, stabilizing agents, wetting agents, emulsifying agents, sweetening agents, coloring agents, flavoring agents, salts for varying the osmotic pressure, buffers, coating agents or antioxidants. They can also contain still other therapeutically valuable substances.

As mentioned above, medicaments containing a compound of formula I and a therapeutically inert excipient are also an aspect of the present invention.

As also mentioned above, the compounds of formula I and their pharmaceutically acceptable acid addition salts can be used in the control or prevention of illnesses and especially in the control of convulsions and anxiety states and/or in the partial or complete antagonism of some or all activities which 1,4-benzodiazepines having tranquillizing activity or other substances display via the central benzodiazepine receptors. The dosage can vary within wide limits and will, of course, be fitted to the individual requirements in each particular case. In general, in the case of oral administration a daily dosage of about 0. display via the central benzodiazepine receptors. The dosage can vary within wide limits and will, of course, be fitted to the individual requirements in each particular case. In general, in the case of oral administration a daily dosage of about 0.1 mg to 100 mg comes into consideration.

The following Examples are intended to illustrate the present invention in more detail, but are not intended to limit its scope in any manner. All temperatures are given in degrees Celsius.

EXAMPLE 1

(a) 14.14 g (49.5 mmol) of ethyl 5,6-dihydro-5-methyl-6-oxo-4H-imidazo[1,5-a][1,4]benzodiazepine-3-carboxylate in 100 ml of tetrahydrofuran were treated portionwise at the boiling temperature with 1.35 g (62 mmol) of lithium borohydride, whereupon the mixture was boiled at reflux for 6 hours. The reaction mixture was then cooled, a mixture of 20 ml of water and 20 ml of concentrated hydrochloric acid was cautiously added thereto, the mixture was heated, stirred at the boiling temperature for 30 minutes, again cooled and treated with concentrated ammonia until the reaction was alkaline. The organic solvent was distilled off on a rotary evaporator and the aqueous suspension obtained was cooled and filtered. The filter residue was washed with water and dried. There was obtained 4,5-dihydro-3-hydroxymethyl-5-methyl-6H-imidazo[1,5-a][1,4]benzodiazepin-6-one of melting point 219°–221°.

(b) 6.73 g (27.6 mmol) of 4,5-dihydro-3-hydroxymethyl-5-methyl-6H-imidazo[1,5-a][1,4]benzodiazepin-6-one was stirred at room temperature for 4 hours together with 33 g (380 mmol) of manganese dioxide in 100 ml of methylene chloride. The mixture was filtered, the filter residue was rinsed thoroughly with about 1.5 l of methylene chloride and the filtrate was evaporated. There was obtained 5,6-dihydro-5-methyl-6-oxo-4H-imidazo[1,5-a][1,4]benzodiazepine-3—carboxaldehyde of melting point 202°–203°.

(c) 13.50 g of an equimolar mixture of chloromethyltriphenylphosphonium chloride and sodium amide were stirred for 15 minutes with 50 ml of tetrahydrofuran, whereby the temperature rose to 42°. 6.2 g (25.7 mmol) of 5,6-dihydro-5-methyl-6-oxo-4H-imidazo[1,5-a][1,4]benzodiazepine-3-carboxaldehyde were then added portionwise thereto, the mixture was stirred at room temperature for a further hour, filtered and the filtrate was evaporated. After chromatography of the residue on silica gel while eluting with cyclohexane/ether/isopropanol (3:3:1) there was obtained 3-[(Z)-2-chlorovinyl]-4,5-dihydro-5-methyl-6H-imidazo-[1,5-a][1,4]benzodiazepin-6-one of melting point 197°–199°.

EXAMPLE 2

2.20 g (8 mmol) of 3-[(Z)-2-chlorovinyl]-4,5-dihydro-5-methyl-6H-imidazo[1,5-a][1,4]benzodiazepin-6-one were stirred at 145° for 6 hours together with 1.43 ml (9.6 mmol) of 1,8-diazabicyclo[5.4.0]undec-7-ene in 30 ml of N,N-dimethylformamide. The reaction mixture was subsequently poured into water and extracted five times with methylene chloride. The organic extracts were washed five times with water, dried over magnesium sulphate and evaporated. After chromatography of the residue on silica gel while eluting with ethyl acetate and subsequent recrystallization from ethyl acetate there was obtained 3-ethynyl-4,5-dihydro-5-methyl-6H-imidazo[1,5-a][1,4]-benzodiazepin-6-one of melting point 191°–193°.

EXAMPLE 3

100 g of an equimolar mixture of chloromethyltriphenylphosphonium chloride and sodium amide were stirred for 45 minutes in 450 ml of tetrahydrofuran, whereby the temperature rose to 37°. 62.23 g (229.7 mmol) of 7-chloro-5,6-dihydro-5-methyl-6-oxo-4H-imidazo[1,5-a][1,4]benzodiazepine-3-carboxaldehyde were then added portionwise thereto at room temperature and, after completion of the addition, the mixture was stirred for a further 1 hour. The reaction mixture was subsequently filtered and the filtrate was evaporated. After chromatography of the residue on silica gel while eluting with cyclohexane/ether/wasopropanol (3:3:1) there was obtained 7-chloro-3-[(Z)-2-chlorovinyl]-4,5-dihydro-5-methyl-6H-imidazo[1,5-a][1,4]benzodiazepin-6-one of melting point 205°–207°.

EXAMPLE 4

20.2 g (65.5 mmol) of 7-chloro-3-[(Z)-2-chlorovinyl]-4,5-dihydro-5-methyl-6H-imidazo[1,5-a][1,4]benzodiazepine—one was heated to boiling under reflux for 5 hours together with 11.7 ml (78.5 mmol) of 1,8-diazabicyclo[5.4.0]undec-7-ene in 200 ml of N,N-dimethylformamide. The reaction mixture was subsequently poured into 800 ml of water and extracted four time with methylene chloride. The organic extracts were washed four times with water, dried over magnesium sulphate and evaporated. After chromatography of the residue on silica gel while eluting with ethyl acetate and two successive crystallizations from acetonitrile and from ethyl acetate there was obtained 7-chloro-3-ethynyl-4,5-dihydro-5-methyl-6H-imidazo[1,5-a][1,4]benzodiazepin-6-one of melting point 201°–202°.

EXAMPLE 5

2.72 g (10 mmol) of 7-chloro-3-ethynyl-4,5-dihydro-5-methyl-6H-imidazo[1,5-a][1,4]benzodiazepin-6-one was dissolved in 20 ml of N,N-dimethylformamide. 1.31 g (30 mmol) of sodium hydride dispersion (55% in oil) was washed with n-hexane and then introduced at room temperature into the above solution. After 10 minutes 0.95 ml (15 mmol) of methyl iodide was added thereto and the mixture was stirred at room temperature for a further 3 hours. The reaction mixture was poured into 300 ml of water and extracted four times with methylene chloride. The organic extracts were washed four times with water and dried over magnesium sulphate. After chromatography of the residue on silica gel while eluting with ethyl acetate and recrystallization from ethyl acetate, there was obtained 7-chloro-4,5-dihydro-5-methyl-3-(1-propynyl)-6H-imidazo[1,5-a][1,4]benzodiazepin-6-one of melting point 243°–244°.

EXAMPLE 6

6.25 g of an equimolar mixture of methyltriphenylphosphonium bromide and sodium amide was stirred for 15 minutes in 40 ml of tetrahydrofuran. 4.13 g (15 mmol) of 7-chloro-5,6-dihydro-5-methyl-6-oxo-4H-imidazo[1,5-a][1,4]benzodiazepine-3-carboxaldehyde was then added to the yellow suspension, whereby the temperature rose to 43° and the suspension decolorized. The mixture was stirred for a further 1 hour, filtered and the filtrate was evaporated. After chromatography of the residue on silica gel while eluting with cyclohexane/ether/isopropanol (3:3:1) and recrystallization from ethyl acetate there was obtained 7-chloro-4,5-dihydro-5-methyl-3-vinyl-6H-imidazo[1,5-a][1,4]benzodiazepin-6-one of melting point 205°–207°.

EXAMPLE 7

15 g (40.4 mmol) of ethyltriphenylphosphonium bromide was placed in 60 ml of tetrahydrofuran and treated dropwise at −40° with 28 ml (45 mmol) of 1.6 molar butyllithium solution in n-hexane. The orange suspension obtained was stirred at −40° for a further 20 minutes and subsequently a solution of 10 g (36 mmol) of 7-chloro-5,6-dihydro-5-methyl-6-oxo-4H-imidazo[1,5-a][1,4]benzodiazepine-3-carboxaldehyde in 250 ml of tetrahydrofuran was added dropwise thereto within 50 minutes at −40° to −50°. The mixture was stirred at room temperature for a further 2 hours and subsequently filtered. The filtrate was evaporated and chromatographed on silica gel while eluting with cyclohexane/ether/isopropanol (3:3:1). There was obtained 7-chloro-4,5-dihydro-5-methyl-3-[(Z)-propenyl]-6H-imidazo[1,5-a][1,4]benzodiazepin-6-one of melting point 169.5°–170.5° (from ethyl acetate/hexane) and 7-chloro-4,5-dihydro-5-methyl-3-[(E)-propenyl]-6H-imidazo[1,5-a][1,4]benzodiazepin-6-one of melting point 200°–201° (from acetonitrile).

EXAMPLE 8

25 g of an equimolar mixture of chloromethyltriphenylphosphonium chloride and sodium amide was stirred at room temperature in 120 ml of tetrahydrofuran for 20 minutes. 12.9 g (50 mmol) of 8-fluoro-5,6-dihydro-5-methyl-6-oxo-4H-imidazo[1,5-a][1,4]benzodiazepine-3-carboxaldehyde was then added thereto and the mixture was stirred at room temperature for 1 hour and at the boiling temperature for 10 minutes. The mixture was cooled, filtered and the filtrate was evaporated. After chromatography of the residue on silica gel while eluting with cyclohexane/ether/isopropanol (3:3:1) and recrystallization from acetonitrile there was obtained 3-[(Z)-2-chlorovinyl]-8-fluoro-4,5-dihydro-5-methyl-6H-imidazo[1,5-a][1,4]benzodiazepine-one of melting point 220°–221°.

EXAMPLE 9

3.70 g (12.7 mmol) of 3-[(Z)-2-chlorovinyl]-8-fluoro-4,5-dihydro-5-methyl-6H-imidazo[1,5-a][1,4]benzodiazepin-6-one was heated to boiling under reflux for 4 hours together with 2.26 ml (15.2 mmol) of 1,8-diazabicyclo[5.4.0]undec-7-ene 30 ml of N,N-dimethylformamide. The reaction mixture was subsequently poured into 400 ml of water and extracted five times with methylene chloride. The organic extracts were washed four times with water, dried over magnesium sulphate and evaporated. The residue was dissolved in ethyl acetate, treated with charcoal and recrystallized from ethyl acetate. There was obtained 3-ethynyl-8-fluoro-4,5-dihydro-5-methyl-6H-imidazo[1,5-a][1,4]benzodiazepine-6-one of melting point 207°–208°.

EXAMPLE 10

40.70 g of an equimolar mixture of butyltriphenylphosphonium bromide and sodium amide was stirred at room temperature for 15 minutes in 150 ml of tetrahydrofuran. 20.73 g (80 mmol) of 8-fluoro-5,6-dihydro-5-methyl-6-oxo-4H-imidazo[1,5-a][1,4]benzodiazepine-3-carboxaldehyde was then added thereto, the mixture was stirred at room temperature for a further 1.5 hours, filtered and the filtrate was evaporated. After chromatography of the residue on silica gel while eluting with cyclohexane/ether/isopropanol (3:3:1) and recrystallization from ethyl acetate and n-hexane there was obtained 8-fluoro-4,5-dihydro-5-methyl-3-(1-pentenyl)-6H-imidazo[1,5-a][1,4]-benzodiazepin-6-one of melting point 150°–151°.

EXAMPLE 11

17.5 g of an equimolar mixture of chloromethyltriphenylphosphonium chloride and sodium amide was stirred for 15 minutes in 100 ml of tetrahydrofuran, whereby the temperature rose to 33°. 11.1 g (38.58 mmol) of (S)-8-chloro-12,12a-dihydro-9-oxo-9H,11H-azeto[2,1-c]imidazo[1,5-a][1,4]benzodiazepine-1-carboxaldehyde was then added portionwise thereto, whereby the temperature rose to 45° with the evolution of ammonia. The mixture was stirred at room temperature for a further 1 hour, filtered and the filtrate was evaporated. After chromatography on silica gel while eluting with cyclohexane/ether/isopropanol (3:3:1) and subsequent recrystallization from ethyl acetate there was obtained (S)-8-chloro-1-[(Z)-2-chlorovinyl]-12,12a-dihydro-9H,11H-azeto[2,1-c]imidazo[1,5-a][1,4]benzodiazepin-9-one of melting point 189°–191°.

EXAMPLE 12

2.21 g (6.9 mmol) of (S)-8-chloro-1-[(Z)-2-chlorovinyl]-12,12a-dihydro-9H,11H-azeto[2,1-c]imidazo[1,5-a][1,4]benzodiazepin-9-one was heated to boiling under reflux for 4 hours together with 1.23 ml (8.3 mmol) of 1,8-diazabicyclo[5.4.0]undec-7-ene in 30 ml of N,N-dimethylformamide. The reaction mixture was subsequently poured into 300 ml of water and extracted five times with methylene chloride. The organic extracts were washed four times with water, dried over magnesium sulphate and evaporated. After chromatography on silica gel while eluting with ethyl acetate and subsequent recrystallization from ethyl acetate there was obtained (S)-8-chloro-1-ethynyl-12,12a-dihydro-9H,11H-azeto[2,1-c]imidazo[1,5-a][1,4benzodiazepin-9-one of melting point 249°–250°.

EXAMPLE 13

8.70 g of an equimolar mixture of methyltriphenylphosphonium bromide and sodium amide were stirred for 20 minutes in 60 ml of tetrahydrofuran. 6 g (20 mmol) of (S)-8-chloro-12,12a-dihydro-9-oxo-9H,11H-azeto[2,1-c]imidazo[1,5-a][1,4]benzodiazepine-1-carboxaldehyde was then added portionwise thereto and the mixture was stirred for a further 1 hour. The mixture was subsequently filtered and the filtrate was evaporated. After chromatography of the residue on silica gel while eluting with cyclohexane/ether/isopropanol (3:3:1) and subsequent recrystallization from ethyl acetate there was obtained (S)-8-chloro-12,12a-dihydro-1-vinyl-9H,11H-azeto[2,1-c]imidazo[1,5-a][1,4]benzodiazepin-9-one of melting point 171°–172°.

EXAMPLE 14

15 g of an equimolar mixture of chloromethyltriphenylphosphonium chloride and sodium amide was stirred in 60 ml of tetrahydrofuran for 20 minutes. 10 g (33 mmol) of (S)-8-chloro-11,12,13,13a-tetrahydro-9-oxo-9H-imidazo[1,5-a]pyrrolo[2,1-c][1,4]benzodiazepine-1-carboxaldehyde was then added thereto, whereby the temperature rose rapidly to 54° with the vigorous evolution of ammonia. The mixture was stirred for a further 45 minutes, filtered and evaporated. The residue was chromatographed on silica gel while eluting with cyclohexane/ether/isopropanol (3:3:1). After recrystallization from ethyl acetate there was obtained (S)-8-chloro-1-[(Z)-2-chlorovinyl]-11,12,13,13a-tetrahydro-9H-imidazo[1,5-a]pyrrolo[2,1-c][1,4]benzodiazepine-one of melting point 209°–210°.

EXAMPLE 15

2.5 g (7.5 mmol) of (S)-8-chloro-1-[(Z)-2-chlorovinyl]-11,12,13,13a-tetrahydro-9H-imidazo[1,5-a]pyrrolo[2,1-c][1,4]benzodiazepin-9-one was heated to boiling under reflux for 5 hours together with 1.66 ml (11.2 mmol) of 1,8-diazabicyclo[5.4.0]undec-7-ene in 30 ml of N,N-dimethylformamide. The reaction mixture was subsequently poured into 400 ml of water and the crystals obtained were filtered off. After drying and recrystallization from N,N-dimethylformamide there was obtained (S)-8-chloro-1-ethynyl-11,12,13,13a-tetrahydro-9H-imidazo[1,5-a]pyrrolo[2,1-c][1,4]benzodiazepin-9-one of melting point 324°–325°.

EXAMPLE 16

250 mg (0.85 mmol) of (S)-8-chloro-1-ethynyl-11,12,13,13a-tetrahydro-9H-imidazo[1,5-a]pyrrolo[2,1- c][1,4]benzodiazepin-9-one was suspended in 5 ml of N,N-dimethylformamide. 50 mg (1 mmol) of sodium hydride dispersion (55% in oil) was washed with n-hexane and then introduced into the above suspension. After 10 minutes 0.1 ml (1.5 mmol) of methyl iodide was added thereto and the mixture was stirred at room temperature for a further 4.5 hours. The mixture was poured into 50 ml of water and extracted four times with methylene chloride. The organic extracts were washed four times with water, dried over magnesium sulphate and evaporated. After chromatography of the residue on silica gel while eluting with ethyl acetate and recrystallization from ethyl acetate and hexane there was obtained (S)-8-chloro-11,12,13,13a-tetrahydro-1-propynyl-9H-imidazo[1,5-a]pyrrolo[2,1-c][1,4]benzodiazepin-9-one of melting point 205°–20°.

EXAMPLE 17

20.8 g of an equimolar mixture of methyltriphenylphosphonium bromide and sodium amide were stirred for 20 minutes in 80 ml of tetrahydrofuran. 15.08 g (50 mmol) of (S)-8-chloro-11,12,13,13a-tetrahydro-9-oxo-9H-imidazo[1,5-a]pyrrolo[2,1-c][1,4]benzodiazepine-1-carboxaldehyde was then added portionwise thereto, whereby the temperature rose to 43° with the evolution of ammonia. The mixture was stirred at room temperature for 1 hour, filtered and the filtrate was evaporated. After chromatography of the residue on silica gel while eluting with cyclohexane/ether/isopropanol (3:3:1) and recrystallization from ethyl acetate there was obtained (S)-8-chloro-11,12,13,13a-tetrahydro-1-vinyl-9H-imidazo[1,5-a]pyrrolo[2,1-c][1,4]benzodiazepin-9-one of melting point 213°–215°.

EXAMPLE 18

(a) 2.31 g of 8-fluoro-4,5-dihydro-5-methyl-6H-imidazo[1,5-a][1,4]benzodiazepin-6-one was stirred at 95° for 1.5 hours with 8.88 g (35 mmol) of iodine in 25 ml of N,N-dimethylformamide. The reaction mixture was then poured into 300 ml of water, decolorized with sodium thiosulphate solution and extracted four times with methylene chloride. The organic extracts were washed three times with water, dried over magnesium sulphate and evaporated. After recrystallization of the residue from ethyl acetate there was obtained 8-fluoro-4,5-dihydro-3-iodo-5-methyl-6H-imidazo[1,5-a][1,4]benzodiazepin-6-one of melting point 187°–188°.

(b) 2.08 g (5.9 mmol) of 8-fluoro-4,5-dihydro-3-iodo-5-methyl-6H-imidazo[1,5-a][1,4]benzodiazepin-6-one was mixed in a closeable flask with 50 mg of bis-(triphenylphosphine)-palladium(II) dichloride and 7 mg of copper(I) iodide in 20 ml of diethylamine. The mixture was cooled with an acetone/dry-ice bath and a few drops of propyne were added thereto. The flask was tightly closed and the mixture was stirred at room temperature for 20 hours. The mixture was then again cooled to −70°, the flask was opened and left to warm to room temperature. The reaction mixture was diluted with methylene chloride and washed twice with water. The organic phase was dried over magnesium sulphate and concentrated. After two-fold recrystallization from ethyl acetate there was obtained 8-fluoro-4,5-dihydro-5-methyl-3-(1-propynyl)-6H-imidazo[1,5-a][1,4]benzodiazepine—one of melting point 219°–220°.

EXAMPLE 19

(a) 27.3 g (100 mmol) of (S)-8-chloro-11,12,13,13a-tetrahydro-9H-imidazo[1,5-a]pyrrolo[2,1-c][1,4]benzodiazepin-9-one was stirred at 100° for 3 hours with 88 g (350 mmol) of iodine in 200 ml of N,N-dimethylformamide. The reaction mixture was cooled, the separated product was filtered off, rinsed with ethyl acetate and, after drying, there was obtained (S)-8-chloro-11,12,13,13a-tetrahydro-1-iodo-9H-imidazo[1,5-a]pyrrolo[2,1-c][1,4]benzodiazepin-9-one of melting point 298°–300°.

(b) 3.0 g (7.5 mmol) of (S)-8-chloro-11,12,13,13a-tetrahydro-1-iodo-9H-imidazo[1,5-a]pyrrolo[2,1-c][1,4]benzodiazepine-one, 70 mg of bis-(triphenylphosphine)-palladium(II) dichloride and 10 mg of copper(I) iodide were cooled with 30 ml of diethylamine to about −60° in a pressure tube and treated with about 2 ml of propyne. The pressure tube was closed and heated to 100° for 20 hours. After cooling and opening the pressure tube the reaction mixture was taken up in methylene chloride, filtered and the filtrate was washed twice with water. The organic phase was dried over magnesium sulphate and evaporated. After chromatography of the residue on silica gel while eluting with ethyl acetate and crystallization from ethyl acetate and hexane there was obtained (S)-8-chloro-11,12,13,13a-tetrahydro-1-(1-propynyl)-9H-imidazo[1,5-a]pyrrolo-[2,1-c][1,4]benzodiazepin-9-one of melting point 208°–209°.

EXAMPLE 20

(a) 12.38 g (50 mmol) of 7-chloro-4,5-dihydro-5-methyl-6H-imidazo[1,5-a][1,4]benzodiazepin-6-one was stirred at room temperature for 40 minutes with 9.80 g (55 mmol) of N-bromosuccinimide in 80 ml of N,N-dimethylformamide. The reaction mixture was poured into 800 ml of water and the suspension obtained was filtered. The filter residue was rinsed with water and taken up in methylene chloride. The organic phase was dried over magnesium sulphate and evaporated. After chromatography of the residue on silica gel while eluting with ethyl acetate and recrystallization from ethyl acetate and hexane there was obtained 3-bromo-7-chloro-4,5-dihydro-5-methyl-6H-imidazo[1,5-a][1,4]benzodiazepin-6-one of melting point 178°–179°.

(b) 3.26 g (10 mmol) of 3-bromo-7-chloro-4,5-dihydro-5-methyl-6H-imidazo[1,5-a][1,4]benzodiazepin-6-one was heated to boiling under reflux overnight with 1.10 g (12 mmol) of 2-methyl-3-butyn-2-ol, 70 mg of bis-(triphenylphosphine)-palladium(II) dichloride and 10 mg of copper(I) iodide in 20 ml of diethylamine and 15 ml of methylene chloride. The reaction mixture was evaporated and the residue was dissolved in methylene chloride. After chromatography of the solution on silica gel while eluting with ethyl acetate and crystallization from ethyl acetate there was obtained 7-chloro-4,5-dihydro-3-(3-hydroxy-3-methyl-1-butynyl)-5-methyl-6H-imidazo[1,5-a][1,4]benzodiazepin-6-one of melting point 194°–195°.

EXAMPLE 21

3.73 g (10 mmol) of 7-chloro-4,5-dihydro-3-iodo-5-methyl-6H-imidazo[1,5-a][1,4]benzodiazepin-6-one was mixed with 1.10 g (12 mmol) of 2-methyl-3-butyn-2-ol and 20 ml of diethylamine. 70 mg of bis-(triphenylphosphine)-palladium(II) dichloride and 10 mg of copper(I) iodide were then added thereto and the mixture was stirred at room temperature for 60 hours. The reaction mixture was evaporated and the residue was dissolved in methylene chloride. The solution was washed twice with water, dried over magnesium sulphate and evaporated. After recrystallization of the residue from ethyl acetate there was obtained 7-chloro-4,5-dihydro-3-(3-hydroxy-3-methyl-1-butynyl)-5-methyl-6H-imidazo[1,5-a][1,4]benzodiazepin-6-one of melting point 193°–194°.

EXAMPLE 22

660 mg (2 mmol) of 7-chloro-4,5-dihydro-3-(3-hydroxy-3-methyl-1-butynyl)-5-methyl-6H-imidazo[1,5-a][1,4]benzodiazepine-one was heated to boiling under reflux overnight with 80 mg of sodium hydroxide in 10 ml of toluene. After evaporation of the solvent the residue was dissolved in methylene chloride and the solution was washed twice with water, dried over magnesium sulphate and evaporated. After recrystallization of the residue from ethyl acetate there was obtained 7-chloro-3-ethynyl-4,5-dihydro-5-methyl-6H-imidazo[1,5-a][1,4]benzodiazepin-6-one of melting point 200°–201°.

EXAMPLE 23

3.73 g (10 mmol) of 7-chloro-4,5-dihydro-3-iodo-5-methyl-6H-imidazo[1,5-a][1,4]benzodiazepin-6-one was stirred at the boiling temperature for 24 hours with 1.46 ml (12 mmol) of 3,3-dimethyl-1-butyne, 70 mg of bis-(triphenylphosphine)-palladium(II) dichloride and 10 mg of copper(I) iodide in 30 ml of diethylamine. After evaporation of the reaction mixture the residue was taken up in methylene chloride and washed twice with water. The organic phase was dried over magnesium sulphate, evaporated and the residue was chromatographed on silica gel while eluting with cyclohexane/ether/isopropanol (3:3:1). After crystallization from ethyl acetate and hexane there was obtained 7-chloro-3-(3,3-dimethyl-1-butynyl)-4,5-dihydro-5-methyl-6H-imidazo[1,5-a][1,4]benzodiazepin-6-one of melting point 126°–128°.

EXAMPLE 24

3.73 g (10 mmol) of 7-chloro-4,5-dihydro-3-iodo-5-methyl-6H-imidazo[1,5-a][1,4]benzodiazepin-6-one was stirred at room temperature for 20 hours with 1.12 g (11 mmol) of phenylacetylene, 70 mg of bis-(triphenylphosphine)-palladium(II) dichloride and 10 mg of copper(I) iodide in 20 ml of diethylamine. The reaction mixture was diluted with methylene chloride and washed twice with water. The organic phase was dried over magnesium sulphate and evaporated. After recrystallization of the residue from ethyl acetate there was obtained 7-chloro-4,5-dihydro-5-methyl-3-(phenylethynyl)-6H-imidazo[1,5-a][1,4]benzodiazepin-6-one of melting point 205°–206°.

EXAMPLE 25

(a) 19.1 g (56.8 mmol) of 7-bromo-5,6-dihydro-5-methyl-6-oxo-4H-imidazo[1,5-a][1,4]benzodiazepine-3-carboxylic acid are decarboxylated at 290°–300°. The melt was taken up in methylene chloride, the solution was diluted with ethyl acetate and ethanol and decolorized with animal charcoal. After evaporation and recrystallization from ethyl acetate and ethanol there was obtained 7-bromo-4,5-dihydro-5-methyl-6H-imidazo[1,5-a][1,4]benzodiazepin-6-one of melting point 196°–197°.

(b) 12.80 g (44 mmol) of 7-bromo-4,5-dihydro-5-methyl-6H-imidazo[1,5-a][1,4]benzodiazepin-6-one was stirred at 95° for 3.5 hours with 39 g (154 mmol) of iodine in 80 ml of N,N-dimethylformamide. The reaction mixture was evaporated, the residue was taken up in methylene chloride and water and decolorized by the addition of sodium thiosulphate. The mixture was filtered and the filtrate was evaporated. After chromatography of the residue on silica gel while eluting with ethyl acetate and recrystallization from methylene chloride and ethyl acetate there was obtained 7-bromo-4,5-dihydro-3-iodo-5-methyl-6H-imidazo[1,5-a][1,4]benzodiazepin-6-one of melting point 203°–204°.

(c) 3.74 g (8.95 mmol) of 7-bromo-4,5-dihydro-3-iodo-5-methyl-6H-imidazo[1,5-a][1,4]benzodiazepin-6-one was stirred at the boiling temperature for 1.5 hours with 0.80 g (9.5 mmol) of 2-methyl-3-butyn-2-ol, 70 mg of bis-(triphenylphosphine)-palladium(II) dichloride and 10 mg of copper(I) iodide in 30 ml of diethylamine. The reaction mixture was evaporated and the residue was chromatographed on silica gel while eluting with ethyl acetate. After recrystallization of the residue, which remains behind upon evaporation of the eluate, from ethyl acetate there was obtained 7-bromo-4,5-dihydro-3-(3-hydroxy-3-methyl-1-butynyl)-5-methyl-6H-imidazo[1,5-a][1,4]benzodiazepin-6-one of melting point 207°–208°.

EXAMPLE 26

(a) 109.03 g (300 mmol) of (S)-8-bromo-11,12,13,13a-tetrahydro-9-oxo-9H-imidazo[1,5-a]pyrrolo[2,1-c][1,4]benzodiazepine-1-carboxylic acid was decarboxylated at 290°. The melt was dissolved in about 400 ml of N,N-dimethylformamide and the solution was poured into 2.5 l of water. After stirring for 30 minutes the precipitated product was filtered off, rinsed with water and dried. There was obtained (S)-8-bromo-11,12,13,13a-tetrahydro-9H-imidazo[1,5-a]pyrrolo[2,1-c][1,4]benzodiazepine-one of melting point 232°–233°.

(b) 15.90 g (50 mmol) of (S)-8-bromo-11,12,13,13a-tetrahydro-9H-imidazo[1,5-a]pyrrolo[2,1-c][1,4]benzodiazepin-9-one was stirred at 100° for 3 hours with 44 g (175 mmol) of iodine and 14 g (100 mmol) of potassium carbonate in 100 ml of N,N-dimethylformamide. The reaction mixture was poured into 1 l of water and, after stirring for 30 minutes, the precipitated product was filtered off. The filter residue was rinsed with water, dried and recrystallized from N,N-dimethylformamide. There was obtained (S)-8-bromo-11,12,13,13a-tetrahydro-1-iodo-9H-imidazo[1,5-a]pyrrolo[2,1-c][1,4]benzodiazepin-9-one of melting point 301°–303°.

(c) 2.22 g (5 mmol) of (S)-8-bromo-11,12,13,13a-tetrahydro-1-iodo-9H-imidazo[1,5-a]pyrrolo[2,1-c][1,4]benzodiazepine—one was stirred at the boiling temperature under reflux for 8 hours with 0.44 g (5 mmol) of 2-methyl-3-butyn-2-ol, 25 mg of palladium(II) acetate, 100 mg of triphenylphosphine and 10 mg of copper(I) iodide in 20 ml of triethylamine and 20 ml of N,N-dimethylformamide. The reaction mixture was evaporated and the residue was chromatographed on silica gel while eluting with ethyl acetate. After evaporation of the eluate and recrystallization of the residue from ethyl acetate there was obtained (S)-8-bromo-11,12,13,13a-tetrahydro-1-(3-hydroxy-3-methyl-1-butynyl)-9H-imidazo[1,5-a]pyrrolo[2,1-c][1,4]benzodiazepin-9-one of melting point 227°–228°.

EXAMPLE 27

2.83 g (7 mmol) of (S)-8-chloro-11,12,13,13a-tetrahydro-1-iodo-9H-imidazo[1,5-a]pyrrolo[2,1-c][1,4]benzodiazepine—one was stirred at 105° for 60 hours with 1.10 g (11 mmol) of phenylacetylene, 25 mg of palladium(II) acetate, 100 mg of triphenylphosphine and 15 mg of copper(I) iodide in 40 ml of triethylamine and 20 ml of N,N-dimethylformamide. The mixture was then evaporated to dryness and the residue was chromatographed on silica gel while eluting with ethyl acetate. After recrystallization from methylene chloride and ethyl acetate there was obtained (S)-8-chloro-11,12,13,13a-tetrahydro-1-(phenylethynyl)-9H-imidazo[1,5-a]pyrrolo[2,1-c][1,4]benzodiazepin-9-one of melting point 241°–242°.

EXAMPLE 28

3.99 g (10 mmol) of (S)-8-chloro-11,12,13,13a-tetrahydro-1-iodo-9H-imidazo[1,5-a]pyrrolo[2,1-c][1,4]benzodiazepine-one are stirred at 100° overnight with 0.88 g (10.5 mmol) of 2-methyl-3-butyn-2-ol, 25 mg of palladium(II) acetate, 100 mg of triphenylphosphine and 10 mg of copper(I) iodide in 40 ml of triethylamine and 20 ml of N,N-dimethylformamide. The mixture was evaporated to dryness and the residue was chromatographed on silica gel while eluting with ethyl acetate. After recrystallization from ethyl acetate there was obtained (S)-8-chloro-11,12,13,13a-tetrahydro-1-(3-hydroxy-3-methyl-1-butynyl)-9H-imidazo[1,5-a]pyrrolo[2,1-c][1,4]benzodiazepin-9-one of melting point 234°–235°.

EXAMPLE 29

4.18 g (10 mmol) of 7-bromo-4,5-dihydro-3-iodo-5-methyl-6H-imidazo[1,5-a][1,4]benzodiazepin-6-one was heated to boiling under reflux for 2 hours with 1.12 g (11 mmol) of phenylacetylene, 70 mg of bis-(triphenylphosphine)-palladium(II) dichloride and 10 mg of copper(I) iodide in 30 ml of diethylamine. The solvent was then evaporated and the residue was chromatographed on silica gel while eluting with ethyl acetate. After recrystallization from ethyl acetate there was obtained 7-bromo-4,5-dihydro-5-methyl-3-(phenylethynyl)-6H-imidazo[1,5-a][1,4]benzodiazepin-6-one of melting point 207°–209°.

EXAMPLE 30

3.40 g (10 mmol) of 4,5-dihydro-3-iodo-5-methyl-6H-imidazo[1,5-a][1,4]benzodiazepin-6-one was heated to boiling under reflux for 1.5 hours with 0.925 g (11 mmol) of 2-methyl-3-butyn-2-ol, 70 mg of bis-(triphenylphosphine)-palladium(II) dichloride and 10 mg of copper(I) iodide in 30 ml of diethylamine. The solvent was then evaporated and the residue was chromatographed on silica gel while eluting with ethyl acetate. After recrystallization from ethyl acetate there was obtained 4,5-dihydro-3-(3-hydroxy-3-methyl-1-butynyl)-5-methyl-6H-imidazo[1,5-a][1,4]benzodiazepin-6-one of melting point 168°–169°.

EXAMPLE 31

3.90 g (11.5 mmol) of 4,5-dihydro-3-iodo-5-methyl-6H-imidazo[1,5-a][1,4]benzodiazepin-6-one was heated to boiling under reflux for 5 hours with 0.67 g (12 mmol) of propargyl alcohol, 70 mg of bis-(triphenylphosphine)-palladium(II) dichloride and 10 mg of copper(I) iodide in 30 ml of diethylamine. The solvent was then evaporated, the residue was taken up in methylene chloride, the solid was filtered off and rinsed with ethyl acetate. After drying there was obtained 4,5-dihydro-3-(3-hydroxy-1-propynyl)-5-methyl-6H-imidazo[1,5-a][1,4]benzodiazepin-6-one of melting point 240°–241°.

EXAMPLE 32

1.20 g (18.6 mmol) of freshly powdered potassium hydroxide was stirred at room temperature for 5 minutes in 15 ml of dimethyl sulfoxide. 1.65 g (5 mmol) of 7-chloro-4,5-dihydro-3-(3-hydroxy-3-methyl-1-butynyl)-5-methyl-6H-imidazo[1,5-a][1,4]benzodiazepin-6-one and 1.42 g (10 mmol) of methyl iodide were then added thereto in succession, whereby the temperature rises to 35°. The reaction mixture was stirred for 45 minutes and then poured into 50 ml of water. The mixture was extracted five times with methylene chloride, the combined organic phases were dried over magnesium sulphate and evaporated. After crystallization from diisopropyl ether there was obtained 7-chloro-4,5-dihydro-3-(3-methoxy-3-methyl-1-butynyl)-5-methyl-6H-imidazo[1,5-a][1,4]benzodiazepin-6-one of melting point 172°–174°.

EXAMPLE 33

7.47 g (20 mmol) of 7-chloro-4,5-dihydro-3-iodo-5-methyl-6H-imidazo[1,5-a][1,4]benzodiazepin-6-one was heated to boiling under reflux for 4 hours with 1.75 g (25 mmol) of 3-butyn-2-ol, 70 mg of bis-(triphenylphosphine)-palladium(II) dichloride and 10 mg of copper(I) iodide in 50 ml of diethylamine and 20 ml of ethylene chloride. After removal of the solvent by evaporation the residue was taken up in methylene chloride and the thus-obtained suspension was suction filtered. The material obtained was washed with methylene chloride and, after recrystallization from ethyl acetate, there was obtained 7-chloro-4,5-dihydro-3-(3-hydroxy-1-butynyl)-5-methyl-6H-imidazo[1,5-a][1,4]benzodiazepin-6-one of melting point 251°–252°.

EXAMPLE 34

3.73 g (10 mmol) of 7-chloro-4,5-dihydro-3-iodo-5-methyl-6H-imidazo[1,5-a][1,4]benzodiazepin-6-one was heated to boiling under reflux for 2 hours with 1.40 g (12.5 mmol) of 3-ethyl-1-pentyn-3-ol, 70 mg of bis-(triphenylphosphine)-palladium(II) dichloride and 10 mg of copper(I) iodide in 30 ml of diethylamine. The reaction mixture was evaporated and the residue was chromatographed on silica gel while eluting with ethyl acetate. After recrystallization from ethyl acetate there was obtained 7-chloro-3-(3-ethyl-3-hydroxy-1-pentynyl)-4,5-dihydro-5-methyl-6H-imidazo[1,5-a][1,4]benzodiazepin-6-one of melting point 186°–188°.

EXAMPLE 35

9.57 g (25.5 mmol) of 7-chloro-4,5-dihydro-3-iodo-5-methyl-6H-imidazo[1,5-a][1,4]benzodiazepin-6-one was heated to boiling under reflux for 3 hours with 3.52 g (32 mmol) of 1-ethynylcyclopentanol, 170 mg of bis-(triphenylphosphine)-palladium(II) dichloride and 30 mg of copper(I) iodide in 60 ml of diethylamine. The reaction mixture was evaporated and the residue was chromatographed on silica gel while eluting with ethyl acetate. After crystallization from ethyl acetate there was obtained 7-chloro-4,5-dihydro-3-[(1-hydroxycyclopentyl)ethynyl]-5-methyl-6H-imidazo[1,5-a][1,4]benzodiazepin-6-one of melting point 207°–208°.

EXAMPLE 36

3.73 g (10 mmol) of 7-chloro-4,5-dihydro-3-iodo-5-methyl-6H-imidazo[1,5-a][1,4]benzodiazepin-6-one was heated to boiling under reflux for 5 hours with 1.09 g (13 mmol) of ethynyl-ethyl carbinol, 70 mg of bis-(triphenylphosphine)-palladium(II) dichloride and 10 mg of copper(I) iodide in 30 ml of diethylamine. The reaction mixture was evaporated and the residue was chromatographed on silica gel while eluting with ethyl acetate. After recrystallization from ethyl acetate there was obtained 7-chloro-4,5-dihydro-3-(3-hydroxy-1-pentynyl)-5-methyl-6H-imidazo[1,5-a][1,4]benzodiazepin-6-one of melting point 178°.

EXAMPLE 37

10.0 g (26.7 mmol) of 7-chloro-4,5-dihydro-3-iodo-5-methyl-6H-imidazo[1,5-a][1,4]benzodiazepin-6-one, 140 mg of bis-(triphenylphosphine)-palladium(II) dichloride, 40 mg of copper(I) iodide and 3.4 ml (40.3 mmol) of methyl propargyl ether in 100 ml of diethylamine were heated to boiling under reflux for 3.5 hours. The reaction mixture was evaporated and the residue was chromatographed on silica gel while eluting with ethyl acetate. After recrystallization from ethyl acetate there was obtained 7-chloro-4,5-dihydro-3-(3-methoxy-1-propynyl)-5-methyl-6H-imidazo[1,5-a][1,4]benzodiazepin-6-one of melting point 154°-156°.

EXAMPLE 38

3.73 g (10 mmol) of 7-chloro-4,5-dihydro-3-iodo-5-methyl-6H-imidazo[1,5-a][1,4]benzodiazepin-6-one was heated to 100° in a pressure tube for 20 hours with 0.87 g of 3-methyl-1-butyne, 70 mg of bis-(triphenylphosphine)-palladium(II) dichloride and 19 mg of copper(I) iodide in 20 ml of diethylamine and 10 ml of ethylene chloride. By evaporation of the reaction mixture and chromatography of the residue on silica gel while eluting with ethyl acetate there was obtained a mixture of product and starting material of about 2:1. In order to remove the starting material, the mixture was heated under reflux the reaction mixture and chromatography of the residue on silica gel while eluting with ethyl acetate there was obtained a mixture of product and starting material of about 2:1. In order to remove the starting material, the mixture was heated under reflux for 5 hours with 0.8 ml of 2-methyl-3-butyn-2-ol, 70 mg of bis-(triphenylphosphine)-palladium(II) dichloride and 15 mg of copper(I) iodide in 15 ml of diethylamine. By evaporation of the reaction mixture and chromatography of the residue on silica gel while eluting with ethyl acetate the byproduct can be separated from the desired product. After recrystallization from ether there was obtained 7-chloro-4,5-dihydro-5-methyl-3-(3-methyl-1-butynyl)-6H-imidazo[1,5-a][1,4]benzodiazepin-6-one of melting point 128°-130°.

EXAMPLE 39

3.37 g (10 mmol) of 7-chloro-4,5-dihydro-3-iodo-5-methyl-6H-imidazo[1,5-a][1,4]benzodiazepin-6-one was heated to 75° for 16 hours with 1.47 g of cyclopropylacetylene, 70 mg of bis-(triphenylphosphine)-palladium(II) dichloride and 20 mg of copper(I) iodide in 20 ml of diethylamine and 10 ml of ethylene chloride. By evaporation of the reaction mixture and chromatography of the residue on silica gel while eluting with ethyl acetate there was obtained a mixture of product and starting material. In order to remove the starting material, the mixture was heated under reflux for 4 hours with 1 ml of 2-methyl-3-butyn-2-ol, 70 mg of bis-(triphenylphosphine)-palladium(II) dichloride and 20 mg of copper(I) iodide in 10 ml of diethylamine and 10 ml of ethylene chloride. By evaporation of the reaction mixture and chromatography of the residue on silica gel while eluting with ethyl acetate the byproduct can be separated from the desired product. After crystallization from ethyl acetate there was obtained 7-chloro-3-(cyclopropylethynyl)-4,5-dihydro-5-methyl-6H-imidazo[1,5-a][1,4]benzodiazepin-6-one of melting point 177°-178°.

EXAMPLE 40

4.07 g (15 mmol) of 7-chloro-3-ethynyl-4,5-dihydro-5-methyl-6H-imidazo[1,5-a][1,4]benzodiazepin-6-one was suspended in 30 ml of tetrahydrofuran and treated dropwise within 35 minutes at a maximum of −5° with 20 ml (30 mmol) of 1.6M butyllithium in hexane. After stirring in an ice-bath for 1.5 hours the mixture was cooled to −74° and there are added thereto 5 ml of hexamethylphosphoric acid triamide and, after 10 minutes, 3.30 g (30 mmol) of dicyclopropyl ketone. The mixture was left to come to room temperature during 6 hours and was stirred over the weekend. The reaction mixture was then poured into 200 ml of water, acidified to pH 7 with 4N hydrochloric acid and extracted four times with ethyl acetate. The combined organic extracts were washed twice with water, dried over magnesium sulphate and evaporated. After chromatography of the residue on silica gel while eluting with methylene chloride/methanol (19:1) and subsequent recrystallization from ethyl acetate there was obtained 7-chloro-3-(3,3-dicyclopropyl-3-hydroxy-1-propynyl)-4,5-dihydro-5-methyl-6H-imidazo[1,5-a][1,4]benzodiazepin-6-one of melting point 179°-181°.

EXAMPLE 41

2.72 g (10 mmol) of 7-chloro-3-ethynyl-4,5-dihydro-5-methyl-6H-imidazo[1,5-a][1,4]benzodiazepin-6-one was suspended in 30 ml of methanol and cooled to 10°. There were then added simultaneously thereto in portions within about 10 minutes 5 ml of 28% sodium hydroxide solution and 3 g of iodine. After stirring at room temperature for 1 hour the suspension was diluted with about 30 ml of water, suction filtered and the suction filter cake was dried. By two recrystallizations from methylene chloride and ethyl acetate and from dioxane there was obtained 7-chloro-4,5-dihydro-3-(2-iodoethynyl)-5-methyl-6H-imidazo[1,5-a][1,4]benzodiazepin-6-one of melting point 215°-216°.

EXAMPLE 42

4.0 g (69.5 mmol) of freshly powdered potassium hydroxide was stirred for 10 minutes in 40 ml of N,N-dimethylformamide and cooled to 10°. 5.48 g (17.3 mmol) of 7-chloro-4,5-dihydro-3-(3-hydroxy-1-butynyl)-5-methyl-6H-imidazo[1,5-a][1,4]benzodiazepin-6-one and 4.94 g (35 mmol) of methyl iodide were added thereto in succession, the ice-bath was removed and the mixture was stirred for a further 1 hour. The reaction mixture was poured into 200 ml of water and extracted five times with methylene chloride. The combined organic extracts were washed four times with water, dried over magnesium sulphate and evaporated. After recrystallization of the residue from ethyl acetate there was obtained 7-chloro-4,5-dihydro-3-(3-methoxy-1-butynyl)-5-methyl-6H-imidazo[1,5-a][1,4]-benzodiazepin-6-one of melting point 139°-141°.

EXAMPLE 43

2.35 g (42 mmol) of freshly powdered potassium hydroxide was stirred in 30 ml of dimethyl sulfoxide for 5 minutes. There were then added in succession 4.0 g (11.25 mmol) of 7-chloro-4,5-dihydro-3-[(1-hydroxycyclopentyl)ethynyl]-5-methyl-6H-imidazo[1,5-a][1,4]benzodiazepine-one and 3.12 g (22.5 mmol) of methyl iodide and the mixture was stirred for a further 1 hour before the dimethyl sulfoxide was removed by evaporation. The residue was taken up in water and extracted three times with methylene chloride. The combined organic extracts were dried over magnesium sulphate, evaporated and the residue was chromatographed on silica gel while eluting with ethyl acetate/hexane (1:1). After recrystallization from ethyl acetate there was obtained 7-chloro-4,5-dihydro-3-[(1-methoxycyclopentyl)ethynyl]-5-methyl-6H-imidazo[1,5-a][1,4]-benzodiazepin-6-one of melting point 174°–175°.

EXAMPLE 44

(a) 3.73 g (10 mmol) of 7-chloro-4,5-dihydro-3-iodo-5-methyl-6H-imidazo[1,5-a][1,4]benzodiazepin-6-one was heated to boiling under reflux for 3 hours with 1.30 g (12.5 mmol) of ethynyltrimethylsilane, 70 mg of bis-(triphenylphosphine)-palladium(II) dichloride and 10 mg of copper(I) iodide in 30 ml of diethylamine. The reaction mixture was evaporated and the residue was chromatographed on silica gel while eluting with ethyl acetate/hexane (1:1). After crystallization from ethyl acetate and hexane there was obtained 7-chloro-4,5-dihydro-5-methyl-3-[(trimethylsilyl)ethynyl]-6H-imidazo[1,5-a][1,4]benzodiazepin-6-one of melting point 186°–187°.

(b) 12.7 g (37 mmol) of 7-chloro-4,5-dihydro-5-methyl-3-[(trimethylsilyl)ethynyl]-6H-imidazo[1,5-a][1,4]benzodiazepine—one was dissolved in 40 ml of methanol and treated with 40 ml of 1N potassium hydroxide solution. After stirring for 1 hour the methanol was distilled off and the aqueous suspension was cooled and suction filtered. After drying there was obtained 7-chloro-3-ethynyl-4,5-dihydro-5-methyl-6H-imidazo[1,5-a][1,4]benzodiazepin-6-one of melting point 194°–195°.

EXAMPLE 45

(a) 3.0 g (10.9 mmol) of 7-chloro-5,6-dihydro-5-methyl-6-oxo-4H-imidazo[1,5-a][1,4]benzodiazepine-3-carboxaldehyde and 5.7 g (21.7 mmol) of triphenylphosphine were dissolved in 80 ml of methylene chloride at room temperature. Thereafter, the mixture was cooled with an ice-bath to 0° and at this temperature there was added dropwise thereto a solution of 4.0 g (12.0 mmol) of tetrabromomethane in 15 ml of methylene chloride. Thereafter, the mixture was stirred at room temperature for a further 6 hours and subsequently evaporated in a vacuum. The residue was suspended in ethyl acetate and heated under reflux for 30 minutes, cooled to 10° while stirring, suction filtered and dried. The crystalline crude product was recrystallized from alcohol and there was obtained 7-chloro-3-(2,2-dibromovinyl)-4,5-dihydro-5-methyl-6H-imidazo[1,5-a][1,4]benzodiazepin-6-one hydrobromide as white crystals of melting point 215°–217°.

(b) 3.3 g (6.44 mmol) of the thus-obtained compound was dissolved in 100 ml of methanol. A solution of 0.31 g (13.48 mmol) of sodium in 30 ml of methanol was added thereto. The reaction mixture was thereafter heated under reflux for 16 hours and subsequently evaporated in a vacuum. The residue was partitioned between water and methylene chloride and the aqueous phase was extracted with methylene chloride. The combined organic phases were washed with water, dried over magnesium sulphate, filtered and evaporated. The residue was dissolved in methylene chloride and chromatographed over 120 g of silica gel (in methylene chloride). Elution was carried out with a mixture of methylene chloride and ethyl acetate in the ratio 9:1, 8:2 and 7:3 (v/v). The fractions which were pure according to thin-layer chromatography were combined and recrystallized from ethyl acetate/hexane. There was obtained 3-(bromoethynyl)-7-chloro-4,5-dihydro-5-methyl-6H-imidazo[1,5-a][1,4]benzodiazepin-6-one as white crystals of melting point >190° (dec.).

EXAMPLE 46

10.3 g (29 mmol) of acetonyltriphenylphosphonium chloride are suspended in 100 ml of tetrahydrofuran under argon. 3.3 g (29.4 mmol) of potassium tert.-butylate was added thereto and the mixture was thereafter stirred at room temperature for a further 30 minutes. After cooling to 10° 4.0 g (14.5 mmol) of 7-chloro-5,6-dihydro-5-methyl-6-oxo-4H-imidazo[1,5-a][1,4]benzodiazepine-3-carboxaldehyde was added thereto and the mixture was stirred at 20° for 1 hour and under reflux for 6 hours. The reaction mixture was evaporated, the residue was partitioned between methylene chloride and water, the organic phase was washed with water and subsequently dried over magnesium sulphate, filtered and evaporated. After chromatography of the residue on silica gel with methylene chloride/ethyl acetate (8:2, 7:3 and 1:1) and subsequent recrystallization of the combined pure fractions from ethyl acetate/hexane there was obtained 7-chloro-4,5-dihydro-3-[(E)-3-oxo-1-butenyl]-5-methyl-6H-imidazo[1,5-a][1,4]benzodiazepin-6-one as white crystals of melting point 235°–237°.

EXAMPLE 47

2.4 g (7.6 mmol) of 7-chloro-4,5-dihydro-3-[(E)-3-oxo-1-butenyl]-5-methyl-6H-imidazo[1,5-a][1,4]benzodiazepin-6-one was dissolved in 50 ml of dimethylformamide while warming. Thereafter, the solution was diluted with 280 ml of ethanol. 0.6 g (15.8 mmol) of sodium borohydride was added to this solution and the mixture was stirred at 20° for 2.5 hours. Thereafter, a further 0.2 g of sodium borohydride was added thereto. After a total reaction period of 4.5 hours the mixture was evaporated in a vacuum. The residue, which still contained dimethylformamide, was poured on to ice/water and stirred at 0° for 1 hour. The crystallizate was filtered off under suction and dried. There was obtained 7-chloro-4,5-dihydro-3-[(E)-3-hydroxy-1-butenyl]-5-methyl-6H-imidazo[1,5-a][1,4]benzodiazepin-6-one as white crystals of melting point 232°–233°.

EXAMPLE 48

3.57 g (10 mmol) of 8-fluoro-4,5-dihydro-3-iodo-5-methyl-6H-imidazo[1,5-a][1,4]benzodiazepin-6-one was heated to boiling under reflux for 6.5 hours with 0.925 g (11 mmol) of 2-methyl-3-butyn-2-ol, 70 mg of bis-(triphenylphosphine)-palladium(II) dichloride and 10 mg of copper(I) iodide in 30 ml of diethylamine. The reaction mixture was then evaporated and the residue was chromatographed on silica gel while eluting with ethyl acetate. After recrystallization from ethyl acetate there was obtained 8-fluoro-4,5-dihydro-3-(3-hydroxy-3-methyl-1-butynyl)-5-methyl-6H-imidazo[1,5-a][1,4]benzodiazepin-6-one of melting point 165°–167°.

EXAMPLE 49

8.93 g (25 mmol) of 8-fluoro-4,5-dihydro-3-iodo-5-methyl-6H-imidazo[1,5-a][1,4]benzodiazepin-6-one was stirred at room temperature for 24 hours with 3.03 g (27 mmol) of 3-ethyl-1-pentyn-3-ol, 100 mg of bis-(triphenylphosphine)-palladium(II) dichloride and 20 mg of copper(I) iodide in 60 ml of diethylamine. A further 0.87 g (7.7 mmol) of 3-ethyl-1-pentyn-3-ol as well as 50 mg of bis-(triphenylphosphine)-palladium(II) dichloride and 50 mg of copper(I) iodide were added thereto and the mixture was stirred at the boiling temperature for 0.5 hour. The reaction mixture was subsequently evaporated and the residue was chromatographed on silica gel while eluting with ethyl acetate. After decolorizing the crude product with active charcoal and crystallization from ethyl acetate there was obtained 8-fluoro-3-(3-ethyl-3-hydroxy-1-pentynyl)-4,5-dihydro-5-methyl-6H-imidazo[1,5-a][1,4]benzodiazepin-6-one of melting point 135°–136°.

EXAMPLE 50

3.57 g (10 mmol) of 8-fluoro-4,5-dihydro-3-iodo-5-methyl-6H-imidazo[1,5-a][1,4]benzodiazepin-6-one was heated to boiling under reflux for 4 hours with 1.22 g (12.5 mmol) of 3-methoxy-3-methyl-1-butyne, 70 mg of bis-(triphenylphosphine)-palladium(II) dichloride and 10 mg of copper(I) iodide in 30 ml of diethylamine. The reaction mixture was evaporated and the residue was chromatographed on silica gel while eluting with ethyl acetate. After recrystallization from ethyl acetate there was obtained 8-fluoro-4,5-dihydro-3-(3-methoxy-3-methyl-1-butynyl)-5-methyl-6H-imidazo[1,5-a][1,4]benzodiazepin-6-one of melting point 149°–150°.

EXAMPLE 51

7 g (19.9 mmol) of 8-fluoro-4,5-dihydro-3-iodo-5-methyl-6H-imidazo[1,5-a][1,4]benzodiazepin-6-one was heated to boiling under reflux for 3 hours with 2.5 ml (29 mmol) of propargyl ether, 100 mg of bis-(triphenylphosphine)-palladium(II) dichloride and 30 mg of copper(I) iodide in 70 ml of diethylamine. The reaction mixture was evaporated and the residue was chromatographed on silica gel while eluting with ethyl acetate. After recrystallization from ethyl acetate there was obtained 8-fluoro-4,5-dihydro-3-(3-methoxy-1-propynyl)-5-methyl-6H-imidazo[1,5-a][1,4]benzodiazepin-6-one of melting point 146°–147°.

EXAMPLE 52

3.6 g (10 mmol) of 8-fluoro-4,5-dihydro-3-iodo-5-methyl-6H-imidazo[1,5-a][1,4]benzodiazepin-6-one was stirred at room temperature for 16 hours with 1.5 g (11 mmol) of p-chlorophenylacetylene, 70 mg of bis-(triphenylphosphine)-palladium(II) dichloride and 15 mg of copper(I) iodide in 35 ml of diethylamine. The reaction mixture was diluted with 175 ml of methylene chloride and washed three times with water. The organic phase was dried over magnesium sulphate and evaporated. By chromatography of the residue on silica gel and subsequent recrystallization from methylene chloride and ethyl acetate there was obtained 3-[(p-chlorophenyl)ethynyl]-8-fluoro-4,5-dihydro-5-methyl-6H-imidazo[1,5-a][1,4]benzodiazepin-6-one of melting point 221°–222°.

EXAMPLE 53

3.6 g (10 mmol) of 8-fluoro-4,5-dihydro-3-iodo-5-methyl-6H-imidazo[1,5-a][1,4]benzodiazepin-6-one was stirred at room temperature overnight with 1.5 g (11 mmol) of o-chlorophenylacetylene, 70 mg of bis-(triphenylphosphine)-palladium(II) dichloride and 15 mg of copper(I) iodide in 20 ml of diethylamine. The reaction mixture was diluted with 175 ml of methylene chloride and washed three times with water. After drying and evaporation of the solution the residue was chromatographed on silica gel while eluting with methylene chloride/methanol (99:1). By recrystallization of the evaporated eluate there was obtained 3-[(o-chlorophenyl)ethynyl]-8-fluoro-4,5-dihydro-5-methyl-6H-imidazo[1,5-a][1,4]benzodiazepin-6-one of melting point 259°–261°.

EXAMPLE 54

1.27 g (5 mmol) of 3-ethynyl-8-fluoro-4,5-dihydro-5-methyl-6H-imidazo[1,5-a][1,4]benzodiazepin-6-one was suspended in 10 ml of tetrahydrofuran and treated dropwise within 20 minutes at a maximum of −5° with 6.4 ml (10 mmol) of 1.6M butyllithium in hexane. After stirring in an ice-bath for 2 hours the mixture was cooled to −70° and there was added thereto in succession 1.7 ml of hexamethylphosphoric acid triamide and 0.6 g (10 mmol) of acetone. The mixture was left to come to room temperature within 4.5 hours, left to stand overnight and poured into about 120 ml of water. After acidification with 4N hydrochloric acid the mixture was extracted four times with ether and six times with ethyl acetate, the combined extracts were dried over magnesium sulphate and evaporated. After chromatography of the residue on silica gel while eluting with ethyl acetate and after crystallization from ethyl acetate there was obtained 8-fluoro-4,5-dihydro-3-(3-hydroxy-3-methyl-1-butynyl)-5-methyl-6H-imidazo[1,5-a][1,4]benzodiazepin-6-one of melting point 163°–164°.

EXAMPLE 55

2.55 g (10 mmol) of 3-ethynyl-8-fluoro-4,5-dihydro-5-methyl-6H-imidazo[1,5-a][1,4]benzodiazepin-6-one was suspended in 20 ml of tetrahydrofuran and treated dropwise within 30 minutes at −5° with 13 ml (20 mmol) of 1.6M butyllithium in hexane. After stirring in an ice-bath for 2 hours the mixture was cooled to −70° and 3.4 ml of hexamethylphosphoric acid triamide and 1.68 g (20 mmol) of cyclopropyl methyl ketone were added thereto in succession. The mixture was left to come to room temperature within 4 hours, stirred overnight and poured into about 200 ml of water. After acidification with 4N hydrochloric acid the mixture was extracted five times with ethyl acetate, the combined extracts were dried over magnesium sulphate and evaporated. The residue was chromatographed on silica gel while eluting with ethyl acetate and after crystallization from ethyl acetate there was obtained 8-fluoro-3-(3-cyclopropyl-3-hydroxy-1-butynyl)-4,5-dihydro-5-methyl-6H-imidazo[1,5-a][1,4]benzodiazepine-one of melting point 191°–192°.

EXAMPLE 56

3.83 g (15 mmol) of 3-ethynyl-8-fluoro-4,5-dihydro-5-methyl-6H-imidazo[1,5-a][1,4]benzodiazepin-6-one was suspended in 30 ml of tetrahydrofuran and treated dropwise within 30 minutes at a maximum of −5° with 20 ml (30 mmol) of 1.6M butyllithium in hexane. After stirring for two hours in an ice-bath the mixture was cooled to −70° and 5 ml of hexamethylphosphoric acid triamide and 2 g (28 mmol) of cyclobutanone was added thereto in succession. The mixture was left to come to room temperature within 5 hours, stirred overnight and poured into 300 ml of water. After acidification with 4N hydrochloric acid the mixture was extracted five times with ethyl acetate. The combined organic extracts were washed with water, dried over magnesium sulphate and evaporated. By chromatography of the residue on silica gel while eluting with ethyl acetate and crystallization from ethyl acetate there was obtained 8-fluoro-4,5-dihydro-3-[(1-hydroxycyclobutyl)-ethynyl]-5-methyl-6H-imidazo[1,5-a][1,4]benzodiazepin-6-one of melting point 177°–179°.

EXAMPLE 57

3.0 g (9.5 mmol) of 8-fluoro-4,5-dihydro-3-(3-hydroxy-3-methyl-1-butynyl)-5-methyl-6H-imidazo[1,5-a][1,4]benzodiazepin-6-one were dissolved in 20 ml of N,N-dimethylformamide and treated at 3° with 2.97 g (19 mmol) of ethyl iodide and 2.13 g of freshly powdered potassium hydroxide (38 mmol). After stirring for 5 minutes the cooling bath was removed and the mixture was left to come to room temperature. The reaction mixture was then poured into 200 ml of water, acidified with 4N hydrochloric acid and extracted four times with methylene chloride. The combined extracts were washed five times with water, dried over magnesium sulphate and evaporated. By recrystallization of the crude product from ethyl acetate and hexane there was obtained 8-fluoro-3-(3-ethoxy-3-methyl-1-butynyl)-4,5-dihydro-5-methyl-6H-imidazo[1,5-a][1,4]benzodiazepin-6-one of melting point 136°–138°.

EXAMPLE 58

(a) 67.8 g (190 mmol) of 8-fluoro-4,5-dihydro-3-iodo-5-methyl-6H-imidazo[1,5-a][1,4]benzodiazepin-6-one was heated to boiling under reflux for 8 hours with 23.4 g (238 mmol) of ethynyltrimethylsilane, 300 mg of bis-(triphenylphosphine)-palladium(II) dichloride and 70 mg of copper(I) iodide in 280 ml of diethylamine and 25 ml of ethylene chloride. The reaction mixture was evaporated and the residue was chromatographed on silica gel while eluting with chloroform/ethyl acetate (3:1). By recrystallization from ethyl acetate there was obtained 8-fluoro-4,5-dihydro-5-methyl-3-[(trimethylsilyl)ethynyl]-6H-imidazo-[1,5-a][1,4]benzodiazepin-6-one of melting point 184°–185°.

(b) In analogy to Example 44(b), from the above compound there was obtained 3-ethynyl-8-fluoro-4,5-dihydro-5-methyl-6H-imidazo[1,5-a][1,4]benzodiazepin-6-one (see Example 9).

EXAMPLE 59

(a) 4.0 g (15.43 mmol) of 8-fluoro-5,6-dihydro-5-methyl-6-oxo-4H-imidazo[1,5-a][1,4]benzodiazepine-3-carboxaldehyde and 8.1 g (30.88 mmol) of triphenylphosphine was dissolved in 150 ml of methylene chloride at room temperature. Thereafter, the mixture was cooled with an ice-bath to 0° and at this temperature there was added dropwise thereto a solution of 5.6 g (16.88 mmol) of tetrabromomethane in 20 ml of methylene chloride. Thereafter, the mixture was stirred at room temperature for a further 4 hours and subsequently evaporated. The suspension obtained was cooled to 0°, suction filtered and dried in a vacuum. The crude product was recrystallized from ethanol. There was obtained 3-(2,2-dibromovinyl)-8-fluoro-4,5-dihydro-5-methyl-6H-imidazo[1,5a][1,4]benzodiazepin-6-one hydrobromide as white crystals of melting point >260° (dec.).

(b) 3.4 g (6.85 mmol) of the above compound was dissolved in 100 ml of methanol. A solution of 0.33 g (14.35 mmol) of sodium in 30 ml of methanol was added thereto. Thereafter, the reaction mixture was heated under reflux for 16 hours and subsequently evaporated in a vacuum. The residue was partitioned between water and methylene chloride and the aqueous phase was extracted with methylene chloride. The combined organic phases were washed with water, dried over magnesium sulphate, filtered and evaporated. The residue was recrystallized from ethyl acetate/hexane. There was obtained 3-(bromoethynyl)-8-fluoro-4,5-dihydro-5-methyl-6H-imidazo[1,5-a][1,4]benzodiazepine-6-one as white crystals of melting point 167°.

EXAMPLE 60

6.78 g (20 mmol) of 4,5-dihydro-3-iodo-5-methyl-6H-imidazo[1,5-a][1,4]benzodiazepin-6-one was heated to 100° in a pressure tube overnight with 80 mg of bis-(triphenylphosphine)-palladium(II) dichloride, 30 mg of copper(I) iodide and about 2 ml of propyne in 60 ml of diethylamine. The reaction mixture was then evaporated and the residue was chromatographed on 300 g of silica gel while eluting with ethyl acetate. By recrystallization of the crude product from ethanol there was obtained 4,5-dihydro-5-methyl-3-(1-propynyl)-6H-imidazo[1,5-a][1,4]benzodiazepin-6-one of melting point 206°–207°.

EXAMPLE 61

6.78 g (20 mmol) of 4,5-dihydro-3-iodo-5-methyl-6H-imidazo[1,5-a][1,4]benzodiazepin-6-one was heated to boiling under reflux for 7 hours with 1.75 g (25 mmol) of 3-butyn-2-ol, 70 mg of bis-(triphenylphosphine)-palladium(II) dichloride and 15 mg of copper(I) iodide in 50 ml of diethylamine and 30 ml of ethylene chloride. The reaction mixture was evaporated and the residue was chromatographed on silica gel while eluting with ethyl acetate. After recrystallization from ethyl acetate and hexane there was obtained 4,5-dihydro-3-(3-hydroxy-1-butynyl)-5-methyl-6H-imidazo[1,5-a][1,4]benzodiazepin-6-one of melting point 161°–162°.

EXAMPLE 62

2.92 g (10 mmol) of 3-bromo-4,5-dihydro-5-methyl-6H-imidazo[1,5-a][1,4]benzodiazepin-6-one was heated to 80° in a pressure tube for 24 hours with 70 mg of bis-(triphenylphosphine)-palladium(II) dichloride, 30 mg of copper(I) iodide and 2.5 ml (20 mmol) of 3,3-dimethyl-1-butyne in 30 ml of diethylamine and 10 ml of ethylene chloride. The reaction mixture was evaporated, the residue was taken up in methylene chloride and washed with water. The organic solution was dried over magnesium sulphate and filtered through a silica gel pad. By crystallization from hexane there was obtained 3-(3,3-dimethyl-1-butynyl)-4,5-dihydro-5-methyl-6H-imidazo[1,5-a][1,4]benzodiazepin-6-one of melting point 148°–150°.

EXAMPLE 63

5.05 g (90 mmol) of freshly powdered potassium hydroxide was suspended in 50 ml of N,N-dimethylformamide and cooled to 3°. 6.0 g (22.5 mmol) of 4,5-dihydro-3-(3-hydroxy-1-propynyl)-5-methyl-6H-imidazo[1,5-a][1,4]benzodiazepin-6-one and 6.39 g (45 mmol) of methyl iodide was added thereto in succession, the ice-bath was removed and the mixture was stirred for a further 1 hour. The reaction mixture was poured into 200 ml of water, acidified to pH 7 with 4N hydrochloric acid and extracted five times with methylene chloride. The combined organic extracts were dried over magnesium sulphate, evaporated and after crystallization of the residue from ethyl acetate there was obtained 4,5-dihydro-3-(3-methoxy-1-propynyl)-5-methyl-6H-imidazo[1,5-a][1,4]benzodiazepin-6-one of melting point 114°–115°.

EXAMPLE 64

4.58 g (80 mmol) of freshly powdered potassium hydroxide was suspended in 65 ml of dimethyl sulfoxide and cooled to 5°. 5.67 g (19.2 mmol) of 4,5-dihydro-3-(3-hydroxy-3-methyl-1-butynyl)-5-methyl-6H-imidazo[1,5-a][1,4]benzodiazepin-6-one and 5.47 g (38.5 mmol) of methyl iodide were added thereto in succession. The cooling bath was removed and the mixture was stirred for a further 1 hour. The reaction mixture was evaporated and the residue was chromatographed on silica gel while eluting with methylene chloride/methanol (19.5:0.5). After crystallization from tert.-butyl methyl ether there was obtained 4,5-dihydro-3-(3-methoxy-3-methyl-1-butynyl)-5-methyl-6H-imidazo[1,5-a][1,4]benzodiazepin-6-one of melting point 136°–137°.

EXAMPLE 65

(a) 14.55 g (43 mmol) of ethyl 7-chloro-8-fluoro-5,6-dihydro-5-methyl-6-oxo-4H-imidazo[1,5-a][1,4]benzodiazepine-3-carboxylate was heated to boiling under reflux for 15 minutes with 1.90 g (45.7 mmol) of sodium hydroxide in 80 ml of ethanol and 30 ml of water. The reaction mixture was then cooled and treated with 10.4 ml of 4N hydrochloric acid. By suction filtering the suspension obtained and drying the product there was obtained 7-chloro-8-fluoro-5,6-dihydro-6-oxo-4H-imidazo[1,5-a][1,4]benzodiazepine-3-carboxylic acid of decomposition point 260°.

(b) 11.64 g (37.5 mmol) of 7-chloro-8-fluoro-5,6-dihydro-6-oxo-4H-imidazo[1,5-a][1,4]benzodiazepine-3-carboxylic acid was heated to 285° in a metal bath until the $CO_2$ cleavage has finished. The melt was poured into 50 ml of ethanol and the precipitated product was filtered off under suction and washed with ethanol. After drying there was obtained 7-chloro-8-fluoro-4,5-dihydro-5-methyl-6H-imidazo[1,5-a][1,4]benzodiazepin-6-one of melting point 234°–235°.

(c) 6.08 g (22.8 mmol) of 7-chloro-8-fluoro-4,5-dihydro-5-methyl-6H-imidazo[1,5-a][1,4]benzodiazepin-6-one was stirred at 100° for 4 hours with 20 g (79.5 mmol) of iodine in 50 ml of N,N-dimethylformamide. The reaction mixture was evaporated, the residue was taken up in methylene chloride and water, decolorized with sodium thiosulphate and neutralized with sodium bicarbonate. The aqueous phase was separated and extracted four times with methylene chloride. The combined organic phases were dried over magnesium sulphate, evaporated and the residue was chromatographed on silica gel while eluting with ethyl acetate/hexane (1:1). There was obtained 7-chloro-8-fluoro-4,5-dihydro-3-iodo-5-methyl-6H-imidazo[1,5-a][1,4]benzodiazepin-6-one of melting point 218°–219°.

(d) 4.40 g (11.2 mmol) of 7-chloro-8-fluoro-4,5-dihydro-3-iodo-5-methyl-6H-imidazo[1,5-a][1,4]benzodiazepin-6-one was heated to boiling under reflux for 1.5 hours with 1.4 g (17 mmol) of 2-methyl-3-butyn-2-ol, 70 mg of bis-(triphenylphosphine)-palladium(II) dichloride and 20 mg of copper(I) iodide in 30 ml of diethylamine. The reaction mixture was evaporated, the residue was dissolved in methylene chloride and methanol and decolorized with active charcoal. By crystallization from methanol there was obtained 7-chloro-8-fluoro-4,5-dihydro-3-(3-hydroxy-3-methyl-1-butynyl)-5-methyl-6H-imidazo[1,5-a][1,4]benzodiazepine—one of melting point 208°–209°.

EXAMPLE 66

(a) 25 g (85 mmol) of ethyl-5,6-dihydro-5,7-dimethyl-6-oxo-4H-imidazo[1,5-a][1,4]benzodiazepine-3-carboxylate was heated to boiling under reflux for 1 hour with 3.40 g (85 mmol) of sodium hydroxide in 200 ml of ethanol and 15 ml of water. After evaporation of the ethanol the residue was diluted with water and acidified with 21 ml of 4N hydrochloric acid. The suspension obtained was suction filtered and washed with water. By drying the filter cake there was obtained 5,6-dihydro-5,7-dimethyl-6-oxo-4H-imidazo[1,5-a][1,4]benzodiazepine-3-carboxylic acid of decomposition point 274°–275°.

(b) 22.20 g (81.8 mmol) of 5,6-dihydro-5,7-dimethyl-6-oxo-4H-imidazo[1,5-a][1,4]benzodiazepine-3-carboxylic acid was heated to 290°–300° in a metal bath until the $CO_2$ cleavage has finished. The melt was dissolved in methylene chloride and ethanol and the solution was concentrated until methylene chloride no longer distilled over. From this solution there crystallized 4,5-dihydro-5,7-dimethyl-6H-imidazo[1,5-a][1,4]benzodiazepin-6-one of melting point 224°–225°.

(c) 15.85 g (69.7 mmol) of 4,5-dihydro-5,7-dimethyl-6H-imidazo[1,5-a][1,4]benzodiazepin-6-one was heated to 95° for 2.5 hours with 67 g (264 mmol) of iodine in 100 ml of N,N-dimethylformamide. The reaction mixture was then poured into 450 ml of water, treated with methylene chloride, decolorized with sodium thiosulphate and neutralized with sodium bicarbonate. The aqueous phase was separated and extracted six times with methylene chloride. The combined organic phases were washed three times with water, dried over magnesium sulphate and evaporated. By chromatography of the residue on silica gel while eluting with ethyl acetate and recrystallization from ethyl acetate and hexane there was obtained 4,5-dihydro-3-iodo-5,7-dimethyl-6H-imidazo[1,5-a][1,4]benzodiazepin-6-one of melting point 106°–108°.

(d) 5 g (14.2 mmol) of 4,5-dihydro-3-iodo-5,7-dimethyl-6H-imidazo[1,5-a][1,4]benzodiazepin-6-one was heated to boiling under reflux for 4.5 hours with 1.50 g (17.8 mmol) of 2-methyl-3-butyn-2-ol, 70 mg of bis-(triphenylphosphine)-palladium(II) dichloride and 20 mg of copper(I) iodide in 40 ml of diethylamine. The reaction mixture was then evaporated and the residue was chromatographed on silica gel while eluting with ethyl acetate. By recrystallization from ethyl acetate there was obtained 4,5-dihydro-3-(3-hydroxy-3-methyl-1-butynyl)-5,7-dimethyl-6H-imidazo[a,5-a][1,4]benzodiazepin-6-one of melting point 165°–167°.

EXAMPLE 67

5.20 g (14 mmol) of 7-chloro-4,5-dihydro-3-iodo-5-methyl-6H-imidazo[1,5-a][1,4benzodiazepin-6-one was heated to boiling under reflux for 4 hours with 1.04 g (18.5 mmol) of propargyl alcohol, 70 mg of bis-(triphenylphosphine)-palladium(II) dichloride and 10 mg of copper(I) iodide in 35 ml of diethylamine. The reaction mixture was evaporated and the residue was suspended in methylene chloride. Tth 1.04 g (18.5 mmol) of propargyl alcohol, 70 mg of bis-(triphenylphosphine)-palladium(II) dichloride and 10 mg of copper(I) iodide in 35 ml of diethylamine. The reaction mixture was evaporated and the residue was suspended in methylene chloride. The suspension was suction filtered and the filter cake was washed with ethyl acetate. After two successive recrystallizations from ethanol and N,N-dimethylformamide, respectively, there was obtained 7-chloro-4,5-dihydro-3-(3-hydroxy-1-propynyl)-5-methyl-6H-imidazo-[1,5-a][1,4]benzodiazepin-6-one of melting point 250°–252°.

EXAMPLE 68

2.0 g (5 mmol) of (S)-8-chloro-11,12,13,13a-tetrahydro-1-iodo-9H-imidazo[1,5-a]pyrrolo[2,1-c][1,4]benzodiazepine-6-one was heated to boiling under reflux for 6 hours with 0.73 g (5.5 mmol) of 4-methoxyphenylacetylene, 50 mg of bis-(triphenylphosphine)-palladium(II) dichloride and 50 mg of copper(I) iodide in 25 ml of diethylamine and 25 ml of N,N-dimethylformamide. The reaction mixture was evaporated and the residue was chromatographed on silica gel while eluting with methylene chloride/methanol (99:1). After recrystallization from methylene chloride and ethyl acetate there was obtained (S)-8-chloro-11,12,13,13a-tetrahydro-1-[(p-methoxyphenyl)ethynyl]-9H-imidazo[1,5-a]pyrrolo[2,1-c][1,4]benzodiazepine-one of melting point 186°–187°.

EXAMPLE 69

2.0 g (5 mmol) (S)-8-chloro-11,12,13,13a-tetrahydro-1-iodo-9H-imidazo[1,5-a]pyrrolo[2,1-c][1,4]benzodiazepin-9-one was heated to boiling under reflux for 9 hours with 0.73 g (5.6 mmol) of 3-methoxyphenylacetylene, 65 mg of bis-(triphenylphosphine)-palladium(II) dichloride and 65 mg of copper(I) iodide in 20 ml of diethylamine and 20 ml of N,N-dimethylformamide. The reaction mixture was evaporated and the residue was chromatographed on silica gel while eluting with methylene chloride/methanol (99:1). By crystallization from methylene chloride and ethyl acetate there was obtained (S)-8-chloro-11,12,13,13a-tetrahydro-1-[(m-methoxyphenyl)ethynyl]-9H-imidazo[1,5-a]pyrrolo[2,1-c][1,4]benzodiazepin-9-one of melting point 204°–205°.

EXAMPLE 70

2.0 g (5 mmol) of (S)-8-chloro-11,12,13,13a-tetrahydro-1-iodo-9H-imidazo[1,5-a]pyrrolo[2,1-c][1,4]benzodiazepine-one was heated to boiling under reflux for 9 hours with 0.75 g (5.5 mmol) of 3-chlorophenylacetylene, 65 mg of bis-(triphenylphosphine)-palladium(II) dichloride and 65 mg of copper(I) iodide in 20 ml of diethylamine and 20 ml of N,N-dimethylformamide. The reaction mixture was evaporated and the residue was chromatographed on silica gel while eluting with methylene chloride/methanol (99.2:0.8). By recrystallization from methylene chloride and ethyl acetate there was obtained (S)-8-chloro-1[(m-chlorophenyl)ethynyl]-11,12,13,13a-tetrahydro-9H-imidazo[1,5-a]pyrrolo[2,1-c][1,4]benzodiazepin-9-one of melting point 207°–209°.

EXAMPLE 71

1.9 g (4.9 mmol) of (S)-8-chloro-11,12,13,13a-tetrahydro-1-iodo-9H-imidazo[1,5-a]pyrrolo[2,1-c][1,4]benzodiazepine-one was heated to boiling under reflux for 3.5 hours with 0.71 g (5.2 mmol) of 2-chlorophenylacetylene, 65 mg of bis-(triphenylphosphine)-palladium(II) dichloride and 65 mg of copper(I) iodide in 25 ml of diethylamine and 25 ml of N,N-dimethylformamide. The reaction mixture was evaporated and the residue was chromatographed on silica gel while eluting with methylene chloride/methanol (99:1). By recrystallization from methylene chloride and ethyl acetate there was obtained (S)-8-chloro-1-[(o-chlorophenyl)ethynyl]-11,12,13,13a-tetrahydro-9H-imidazo[1,5-a]pyrrolo[2,1-c][1,4]benzodiazepine-one of melting point 217°–219°.

EXAMPLE 72

(a) 44.26 g (185 mmol) of (S)-11,12,13,13a-tetrahydro-9H-imidazo[1,5-a]pyrrolo[2,1-c][1,4]benzodiazepin-9-one was stirred at 100° for 4 hours with 162.8 g (645 mmol) of iodine in 300 ml of N,N-dimethylformamide. The reaction mixture was evaporated, the residue was taken up in water and methylene chloride, decolorized with sodium thiosulphate and neutralized with sodium bicarbonate. The aqueous phase was separated and extracted four times with methylene chloride. The combined organic phases were dried over magnesium sulphate and evaporated. By chromatography of the crude product on silica gel while eluting with ethyl acetate and subsequent recrystallization from methylene chloride and methanol there was obtained (S)-11,12,13,13a-tetrahydro-1-iodo-9H-imidazo[1,5-a]pyrrolo[2,1-c][1,4]benzodiazepin-9-one of melting point 222°–223°.

(b) 3.65 g (10 mmol) of (S)-11,12,13,13a-tetrahydro-1-iodo-9H-imidazo[1,5-a]pyrrolo[2,1-c][1,4]benzodiazepin-9-one was heated to boiling under reflux for 1.5 hours with 1.26 g (15 mmol) of 2-methyl-3-butyn-2-ol, 70 mg of bis-(triphenylphosphine)-palladium(II) dichloride and 20 mg of copper(I) iodide in 30 ml of diethylamine. The reaction mixture was evaporated and the residue was chromatographed on silica gel while eluting with ethyl acetate. By recrystallization of the crude product from methanol and water there was obtained (S)-11,12,13,13a-tetrahydro-1-(3-hydroxy-3-methyl-1-butynyl)-9H-imidazo[1,5-a]pyrrolo[2,1-c][1,4]benzodiazepin-9-one of melting point 128°.

EXAMPLE 73

(a) 27 g of 5,6-dihydro-5-methyl-4-oxo-4H-imidazo[1,5-a]thieno[3,2-f][1,4]diazepine-7-carboxylic acid was immersed in a flask filled with argon in a heating bath pre-heated to 280°. The substance melts with decarboxylation. After completion of the evolution of carbon dioxide (about 7 to 8 min.) the flask was cooled slightly. Even before it had solidified, the reaction mixture was mixed with 250 ml of trichloromethane. The solution was evaporated in a vacuum and the residue was recrystallized from ethyl acetate/diisopropyl ether. There was obtained 5,6-dihydro-5-methyl-4H-imidazo[1,5-a]thieno[3,2-f][1,4]diazepine-one of melting point 160°–163°. After recrystallization from ethyl acetate the melting point was 163°–164°.

(b) 22 g of 5,6-dihydro-5-methyl-4H-imidazo[1,5-a]thieno[3,2-f][1,4]diazepine-one was dissolved in 330 ml of dimethylformamide and treated with 50.6 g of iodine. The mixture was stirred at room temperature for 24 hours and then at 30° for 18 hours. It was then poured into 9 l of saturated aqueous sodium hydrogen carbonate solution. This solution was extracted four times with trichloromethane. The trichloromethane solutions were washed in succession with aqueous sodium thiosulphate solution and with aqueous sodium chloride solution, then dried over sodium sulphate and evaporated in a vacuum. The residue was chromatographed through 2.5 kg of silica gel. An impurity was first eluted with trichloromethane. The main product was then eluted with trichloromethane/ethanol mixtures 199:1 and 99:1. These eluates are evaporated in a vacuum and the residue was crystallized several times from ethyl acetate/diisopropyl ether and then from ethyl acetate. There was obtained 5,6-dihydro-7-iodo-5-methyl-4H-imidazo[1,5-a]thieno[3,2-f][1,4]diazepine-one of melting point 175°–177°.

(c) 5.52 g of 5,6-dihydro-7-iodo-5-methyl-4H-imidazo[1,5-a]thieno[3,2-f][1,4]diazepine-one in 30 ml of diethylamine was treated with 1.92 ml of 2-methyl-3-butyn-2-ol, 75 mg of bis-(triphenylphosphine)-palladium(II) chloride and 13 mg of copper(I) iodide. The mixture was stirred at reflux temperature for 2 hours. The reaction mixture was then evaporated in a vacuum. The residue was dissolved in dichloromethane and this solution was washed twice with water. After drying over sodium sulphate this solution was chromatographed through 300 g of silica gel. Unreacted starting material was first recovered with dichloromethane/ethanol mixtures 99:1, 98:2 and 97:3. There was then eluted with dichloromethane/ethanol mixtures 96:4 and 95:5 an oily substance which crystallized from ethyl acelate/diethyl ether. There was obtained 5,6-dihydro-7-(3-hydroxy-3-methyl-1-butynyl)-5-methyl-4H-imidazo[1,5-a]-thieno[3,2-f][1,4]diazepine-one of melting point 180°–181°.

The following products were obtained in an analogous manner:

(d) (S)-10,11,12,12a-Tetrahydro-1-(3-hydroxy-3-methyl-1-butynyl)-8H-imidazo[5,1-c]pyrrolo[1,2-a]thieno[2,3-e][1,4]diazepine-one of melting point 145°–147°;

(e) 4,5-dihydro-3-(3-hydroxy-3-methyl-1-butynyl)-5-methyl-6H-imidazo[1,5-a]thieno[2,3-f][1,4]diazepine-one of melting point 198°–200°;

(f) (S)-10,11,12,12a-tetrahydro-1-(3-hydroxy-3-methyl-1-butynyl)-8H-imidazo[5,1-c]pyrrolo[1,2-a]thieno[3,2-e][1,4]diazepine-one of melting point 142°–144°.

EXAMPLE 74

(a) 5.1 g of 5,6-dihydro-7-iodo-5-methyl-4H-imidazo[1,5-a]thieno[3,2-f][1,4]diazepine-one (prepared in accordance with Example 73) was dissolved in 47 ml of diethylamine and 20 ml of dimethylformamide. 1.75 ml of phenylacetylene, 105 mg of bis-(triphenylphosphine)-palladium(II) chloride and 17 mg of copper(I) iodide were then added. The mixture was stirred at room temperature for 2 hours and then concentrated in a vacuum. The residue was diluted with 200 ml of dichloromethane and washed twice with water. The aqueous washings were extracted twice with dichloromethane. The combined dichloromethane solutions were dried over sodium sulphate and chromatographed through 300 g of silica gel. Elution was carried out first with trichloromethane and trichloromethane/ethanol mixtures 199:1 and 99:1. There was then eluted with a trichloromethane/ethanol mixture 97:3 an oily substance which can be crystallized from isopropanol/water. After repeated recrystallizations from isopropanol/water there was obtained 5,6-dihydro-5-methyl-7-(phenylethynyl)-4H-imidazo[1,5-a]thieno[3,2-f][1,4]diazepine one of melting point 143°–144°.

The following products were obtained in an analogous manner:

(b) (S)-10,11,12,12a-Tetrahydro-1-(phenylethynyl)-8H-imidazo[5,1-c]pyrrolo[1,2-a]thieno[2,3-e][1,4]diazepine-one of melting point 159°–160°;

(c) 4,5-dihydro-5-methyl-3-(phenylethynyl)-6H-imidazo[1,5-a]thieno[2,3-f][1,4]diazepine-one of melting point 200°–202°;

(d) (S)-10,11,12,12a-tetrahydro-1-(phenylethynyl)-8H-imidazo[5,1-c]pyrrolo[1,2-a]thieno[3,2-e][1,4]diazepine-one of melting point 218°–220°.

EXAMPLE A

Tablets of the following composition are prepared in the usual manner:

|  | mg/tablet |
| --- | --- |
| 7-Chloro-4,5-dihydro-3-(3-hydroxy-3--methyl-1-butynyl)-5-methyl-6H—imidazo[1,5-a][1,4]benzodiazepin-6 one | 0.2 |
| Lactose | 140 |
| Maize starch | 50.8 |
| Polyvinylpyrrolidine | 8 |
| Magnesium stearate | 1 |
| Tablet weight | 200 |

EXAMPLE B

Capsules of the following composition are prepared in the usual manner:

|  | mg/capsule |
| --- | --- |
| 7-Chloro-4,5-dihydro-3-(3-hydroxy-3 methyl-1-butynyl)-5-methyl-6H—imidazo-[1,5-a][1,4]benzodiazepin-6-one | 0.5 |
| Lactose | 40 |
| Maize starch | 8 |
| Talc | 1 |
| Magnesium stearate | 0.5 |
| Capsule fill weight | 50 |

EXAMPLE C

Injection solutions of the following composition are prepared:

|  |  |
| --- | --- |
| 7-Chloro-4,5-dihydro-5-methyl-3-(1-propynyl)-6H—imidazo-[1,5-a][1,4]benzodiazepin-6-one | 0.1 mg |
| Sodium chloride | 45.0 mg |
| SESQUESTREN Na₂ | 0.5 mg |
| Acetic acid p.a. | 0.5 mg |
| NaOH 1N ad pH 4.5 | q.s. |
| Water for injection q.s. ad | 5.0 ml |

We claim:

1. A compound of the formula

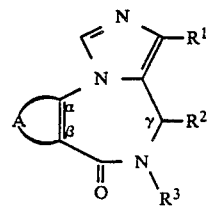

wherein A taken together with the two carbon atoms denoted by α and β are one of the following groups:

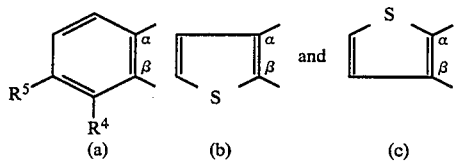

R$^1$ is one of the following groups:
—CH═CH—R$^6$ (d)

and

—C≡C—R$^6$, (e)

R$^2$ is hydrogen and R$^3$ is lower alkyl or R$^2$ and R$^3$ together are dimethylene or trimethylene, R$^4$ and R$^5$ each independently is hydrogen, halogen, trifluoromethyl or lower alkyl, and R$^6$ is hydrogen, halogen, a monocyclic aromatic hydrocarbon group which is unsubstituted or substituted with lower alkyl, lower alkoxy or halogen, or a saturated lower hydrocarbon group which is optionally mono- or di-substituted by hydroxy, lower alkoxy (C$_3$–C$_7$)-cycloalkyl or oxo, whereby the compound has the (S)- or (R,S)-configuration with reference to the carbon atom denoted by γ when R$^2$ and R$^3$ together are dimethylene or trimethylene and whereby the double bond present in group (d) has the E- and/or Z-configuration when R$^6$ is different from hydrogen.

2. A compound in accordance with claim 1, wherein R$^1$ is the group —CH═CH—R$^6$ and R$^6$ is hydrogen, lower alkyl, lower hydroxyalkyl, lower alkoxy-lower alkyl, (C$_3$–C$_7$)-cycloalkyl, hydroxy-(C$_4$–C$_7$)-cycloalkyl, lower alkoxy-(C$_4$–C$_7$)-cycloalkyl, (C$_3$–C$_7$)-cycloalkyl-lower alkyl, phenyl or halogen.

3. A compound in accordance with claim 1, wherein R$^1$ is the group —C≡C—R$^6$ and R$^6$ is hydrogen, lower alkyl, lower hydroxyalkyl, lower alkoxy-lower alkyl, (C$_3$–C$_7$)-cycloalkyl, hydroxy-(C$_4$–C$_7$)-cycloalkyl, lower alkoxy-(C$_4$–C$_7$)-cycloalkyl, (C$_3$–C$_7$)-cycloalkyl-lower alkyl or phenyl.

4. A compound in accordance with claim 1, wherein R$^1$ is the group —C≡C—R$^6$ and R$^6$ is hydrogen, lower alkyl, lower hydroxyalkyl, lower alkoxyalkyl, (C$_3$–C$_7$)-cycloalkyl, hydroxy-(C$_4$–C$_7$)-cycloalkyl, lower alkoxy-(C$_4$–C$_7$)-cycloalkyl, (C$_3$–C$_7$)-cycloalkyl-lower alkyl, (C$_3$–C$_7$)-cycloalkyl-lower hydroxyalkyl or (C$_3$–C$_7$)-cycloalkyl-lower alkoxyalkyl.

5. A compound in accordance with claim 4, wherein R$^6$ is hydrogen, lower alkyl, lower 1-hydroxyalkyl, lower 1-alkoxyalkyl, (C$_3$–C$_7$)-cycloalkyl, 1-hydroxy-(C$_4$–C$_7$)-cycloalkyl, 1-(lower alkoxy)-(C$_4$–C$_7$)-cycloalkyl or 1-[(C$_3$–C$_7$)-cycloalkyl]-lower 1-hydroxyalkyl.

6. A compound in accordance with claim 5, wherein R$^6$ is lower alkyl, lower 1-hydroxyalkyl or (C$_3$–C$_7$)-cycloalkyl.

7. A compound in accordance with claim 1, wherein R$^2$ is hydrogen and R$^3$ is methyl or R$^2$ and R$^3$ together are dimethylene or trimethylene and the carbon atom denoted by γ has the (S)-configuration.

8. A compound in accordance with claim 1, wherein A is a residue of formula (a) and one of R$^4$ and R$^5$ is hydrogen and the other is hydrogen or halogen.

9. A compound in accordance with claim 8, wherein R$^4$ and R$^5$ both are hydrogen.

10. A compound in accordance with claim 8, wherein R$^4$ is hydrogen and R$^5$ is fluorine.

11. A compound in accordance with claim 8, wherein R$^4$ is chlorine or bromine and R$^5$ is hydrogen.

12. 7-Chloro-4,5-dihydro-5-methyl-3-(1-propynyl)-6H-imidazo[1,5-a][1,4]benzodiazepin-6-one.

13. 7-Chloro-4,5-dihydro-3-(3-hydroxy-3-methyl-1-butynyl)-5-methyl-6H-imidazo[1,5-a][1,4]benzodiazepin-6-one.

14. 7-Bromo-4,5-dihydro-3-(3-hydroxy-3-methyl-1-butynyl)-5-methyl-6H-imidazo[1,5-a][1,4]benzodiazepin-6-one.

15. 7-Chloro-4,5-dihydro-3-(3-hydroxy-1-butynyl)-5-methyl-6H-imidazo[1,5-a][1,4]benzodiazepin-6-one.

16. 4,5-Dihydro-5-methyl-3-(1-propynyl)-6H-imidazo-[1,5-a][1,4]benzodiazepin-6-one.

17. 7-Chloro-4,5-dihydro-5-methyl-3-(3-methyl-1-butynyl)-6H-imidazo[1,5-a][1,4]benzodiazepin-6-one.

18. 7-Chloro-4,5-dihydro-3-(3-hydroxy-1-propynyl)-5-methyl-6H-imidazo[1,5-a][1,4]benzodiazepin-6-one.

19. 7-Chloro-3-(cyclopropylethynyl)-4,5-dihydro-5-methyl-6H-imidazo[1,5-a][1,4]benzodiazepin-6-one.

20. A compound of the formula

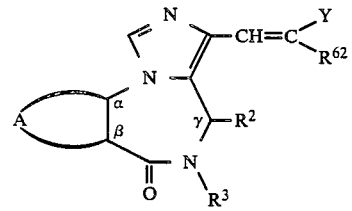

IVa wherein Y and R$^{62}$ are halogen, A taken together with the two carbon atoms denoted by α and β are one of the following groups:

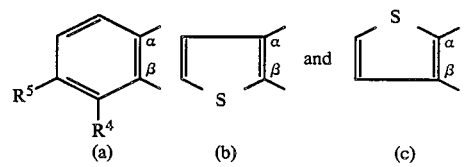

R$^2$ is hydrogen and R$^3$ is lower alkyl or R$^2$ and R$^3$ together are dimethylene or trimethylene, R$^4$ and R$^5$ each independently is hydrogen, halogen, trifluoromethyl or lower alkyl, whereby the compound has the (S)- or (R,S)-configuration with reference to the carbon atom denoted by γ when R$^2$ and R$^3$ together are dimethylene or trimethylene.

21. A compound of the formula

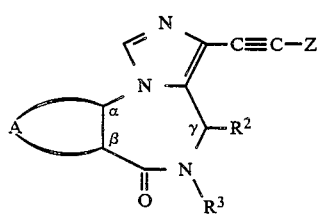

VIII wherein Z is a trialkylsilyl or α-hydroxyalkyl group, A taken together with the two carbon atoms denoted by α and β are one of the following groups:

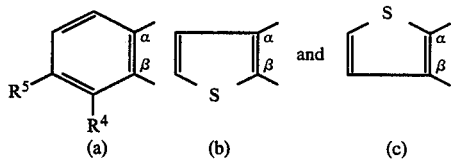

(a) (b) (c)

$R^2$ is hydrogen and $R^3$ is lower alkyl or $R^2$ and $R^3$ together are dimethylene or trimethylene, $R^4$ and $R^5$ each independently is hydrogen, halogen, trifluoromethyl or lower alkyl, whereby the compound has the (S)- or (R,S)-configuration with reference to the carbon atom denoted by γ when $R^2$ and $R^3$ together are dimethylene or trimethylene.

22. A compound of the formula

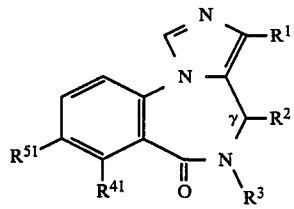　　IX wherein one of $R^{41}$ and $R^{51}$ is amino and the other is hydrogen, halogen, trifluoromethyl or lower alkyl, $R^1$ is one of the following groups:

—CH=CH—$R^6$　　(d)

and

—C≡C—$R^6$,　　(e)

$R^2$ is hydrogen and $R^3$ is lower alkyl or $R^2$ and $R^3$ together are dimethylene or trimethylene, and $R^6$ is hydrogen, halogen, a monocyclic aromatic hydrocarbon group which is unsubstituted or substituted with lower alkyl, lower alkoxy or halogen, or a saturated lower hydrocarbon group which is optionally mono- or di-substituted by hydroxy, lower alkoxy, (C$_3$–C$_7$)-cycloalkyl or oxo, whereby the compound has the (S)- or (R,S)-configuration with reference to the carbon atom denoted by γ when $R^2$ and $R^3$ together are dimethylene or trimethylene and whereby the double bond present in group (d) has the E- and/or Z-configuration when $R^6$ is different from hydrogen.

23. A pharmaceutical composition comprising a pharmaceutically effective amount of a compound of the formula

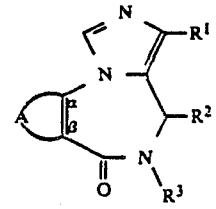

wherein A taken together with the two carbon atoms denoted by α and β are one of the following groups:

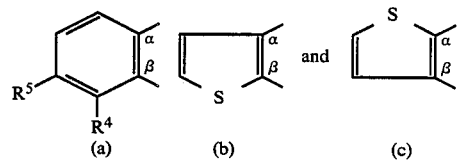

(a) (b) (c)

$R^1$ is one of the following groups:

—CH=CH—$R^6$　　(d)

and

—C≡C—$R^6$,　　(e)

$R^2$ is hydrogen and $R^3$ is lower alkyl or $R^2$ and $R^3$ together are dimethylene or trimethylene, $R^4$ and $R^5$ each independently is hydrogen, halogen, trifluoromethyl or lower alkyl, and $R^6$ is hydrogen, halogen, a monocyclic aromatic hydrocarbon group, unsubstituted or substituted with lower alkyl, lower alkoxy or halogen or a saturated lower hydrocarbon group which is optionally mono-or di-substituted by hydroxy, lower alkoxy, (C$_3$–C$_7$)-cycloalkyl or oxo, whereby the compound has the (S)- or (R,S)-configuration with reference to the carbon atom denoted by γ when $R^2$ and $R^3$ together are dimethylene or trimethylene and whereby the double bond present in group (d) has the E- and/or Z-configuration when $R^6$ is different from hydrogen, and an inert carrier.

24. A composition in accordance with claim 23, wherein $R^1$ is the group —CH=CH—$R^6$ and $R^6$ is hydrogen, lower alkyl, lower hydroxyalkyl, lower alkoxy-lower alkyl, (C$_3$–C$_7$)-cycloalkyl, hydroxy-(C$_4$–C$_7$)-cycloalkyl, lower alkoxy-(C$_4$–C$_7$)-cycloalkyl, (C$_3$–C$_7$)-cycloalkyl-lower alkyl, phenyl or halogen.

25. A composition in accordance with claim 23, wherein $R^1$ is the group —C≡C—$R^6$ and $R^6$ is hydrogen, lower alkyl, lower hydroxyalkyl, lower alkoxy-lower alkyl, (C$_3$–C$_7$)-cycloalkyl, hydroxy-(C$_4$–C$_7$)-cycloalkyl, lower alkoxy-(C$_4$–C$_7$)-cycloalkyl, (C$_3$–C$_7$)-cycloalkyl-lower alkyl or phenyl.

26. A composition in accordance with claim 23, wherein $R^1$ is the group —C≡C—$R^6$ and $R^6$ is hydrogen, lower alkyl, lower hydroxyalkyl, lower alkoxyalkyl, (C$_3$–C$_7$)-cycloalkyl, hydroxy-(C$_4$–C$_7$)-cycloalkyl, lower alkoxy-(C$_4$–C$_7$)-cycloalkyl, (C$_3$–C$_7$)-cycloalkyl-lower alkyl, (C$_3$–C$_7$)-cycloalkyl-lower hydroxyalkyl or (C$_3$–C$_7$)-cycloalkyl-lower alkoxyalkyl.

27. A composition in accordance with claim 26, wherein $R^6$ is hydrogen, lower alkyl, lower 1-hydroxyalkyl, lower 1-alkoxyalkyl, (C$_3$–C$_7$)-cycloalkyl, 1-hydroxy-(C$_4$–C$_7$)-cycloalkyl, 1-(lower alkoxy)-(C$_4$–C$_7$)-cycloalkyl or 1-[(C$_3$–C$_7$)-cycloalkyl]-lower 1-hydroxyalkyl.

28. A composition in accordance with claim 27, wherein $R^6$ is lower alkyl, lower 1-hydroxyalkyl or $(C_3-C_7)$-cycloalkyl.

29. A composition in accordance with claim 23, wherein $R^2$ is hydrogen and $R^3$ is methyl or $R^2$ and $R^3$ together are dimethylene or trimethylene and the carbon atom denoted by $\gamma$ has the (S)-configuration.

30. A composition in accordance with claim 23, wherein A is a residue of formula (a) and one of $R^4$ and $R^5$ is hydrogen and the other is hydrogen or halogen.

31. A composition in accordance with claim 30, wherein $R^4$ and $R^5$ both are hydrogen.

32. A composition in accordance with claim 30, wherein $R^4$ is hydrogen and $R^5$ is fluorine.

33. A composition in accordance with claim 30, wherein $R^4$ is chlorine or bromine and $R^5$ is hydrogen.

* * * * *

UNITED STATES PATENT AND TRADEMARK OFFICE
CERTIFICATE OF CORRECTION

PATENT NO.  : 4,863,920
DATED       : September 5, 1989
INVENTOR(S) : Walter Hunkeler, Emilio Kyburz and Marc Meier It is certified that error appears in the above-identified patent and that said Letters Patent is hereby corrected as shown below:

Column 38, Claim 23, lines 1-9, delete

"  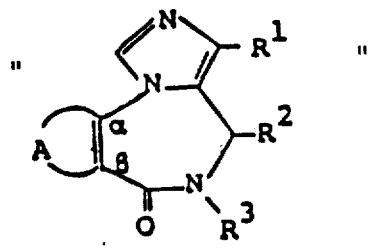  "

and insert thereof   -- 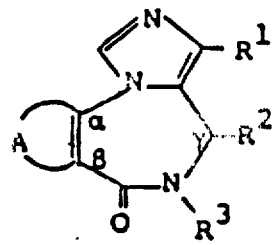   I  --

Signed and Sealed this

Twenty-third Day of June, 1992

Attest:

DOUGLAS B. COMER

Attesting Officer      Acting Commissioner of Patents and Trademarks